US010221233B2

(12) United States Patent
Corthésy et al.

(10) Patent No.: US 10,221,233 B2
(45) Date of Patent: Mar. 5, 2019

(54) COMPOSITIONS COMPRISING SECRETORY-LIKE IMMUNOGLOBULINS

(71) Applicant: CSL BEHRING AG, Bern (CH)

(72) Inventors: Blaise Corthésy, Thierrens (CH); Stéphanie Longet, Dublin (IE); Marius Loetscher, Gerzensee (CH); Sylvia Miescher, Bern (CH); Adrian Zuercher, Bern (CH)

(73) Assignee: CSL BEHRING AG, Bern (CH)

( * ) Notice: Subject to any disclaimer, the term of this patent is extended or adjusted under 35 U.S.C. 154(b) by 574 days.

(21) Appl. No.: 14/380,521

(22) PCT Filed: Mar. 8, 2013

(86) PCT No.: PCT/EP2013/054697
§ 371 (c)(1),
(2) Date: Aug. 22, 2014

(87) PCT Pub. No.: WO2013/132052
PCT Pub. Date: Sep. 12, 2013

(65) Prior Publication Data
US 2015/0056180 A1 Feb. 26, 2015

(30) Foreign Application Priority Data

Mar. 9, 2012 (EP) .................................... 12158931
May 16, 2012 (EP) .................................... 12168343

(51) Int. Cl.
*A61K 39/395* (2006.01)
*C07K 16/00* (2006.01)
*C07K 16/06* (2006.01)
*C07K 16/18* (2006.01)
*C07K 14/735* (2006.01)
*C07K 1/14* (2006.01)
*B01D 15/38* (2006.01)
*A61K 39/00* (2006.01)

(52) U.S. Cl.
CPC ........ *C07K 16/00* (2013.01); *C07K 14/70535* (2013.01); *C07K 16/065* (2013.01); *C07K 16/18* (2013.01); *A61K 2039/505* (2013.01); *B01D 15/3804* (2013.01); *C07K 1/14* (2013.01); *C07K 2317/21* (2013.01); *C07K 2319/036* (2013.01); *C07K 2319/10* (2013.01); *C07K 2319/32* (2013.01)

(58) Field of Classification Search
None
See application file for complete search history.

(56) References Cited

U.S. PATENT DOCUMENTS

| | | |
|---|---|---|
| 5,258,177 A | 11/1993 | Uemura et al. |
| 5,410,025 A | 4/1995 | Moller et al. |
| 5,500,345 A | 3/1996 | Soe et al. |
| 6,069,236 A | 5/2000 | Burnouf-Radosevich et al. |
| 6,300,104 B1 | 10/2001 | Morrison et al. |
| 6,307,028 B1 | 10/2001 | Lebing et al. |
| 6,646,108 B1 | 11/2003 | Leibl et al. |
| 6,696,620 B2 | 2/2004 | Hiatt et al. |
| 6,967,106 B2 | 11/2005 | Simon |
| 7,597,891 B2 | 10/2009 | Simon |
| 7,749,721 B2 | 7/2010 | Alonso-Garcia et al. |
| 7,794,721 B2 | 9/2010 | Simon |
| 8,021,645 B2 | 9/2011 | Simon et al. |
| 8,119,104 B2 | 2/2012 | Simon et al. |
| 8,313,730 B2 | 11/2012 | Simon et al. |
| 8,709,413 B2 | 4/2014 | Simon |
| 9,505,847 B2 | 11/2016 | Cassan et al. |
| 9,522,184 B2 | 12/2016 | Von Gunten et al. |
| 9,546,209 B2 | 1/2017 | Aebi et al. |
| 2003/0082643 A1 | 5/2003 | Hudson et al. |
| 2004/0132979 A1 | 7/2004 | Chtourou et al. |
| 2004/0199945 A1 | 10/2004 | Hiatt et al. |
| 2008/0145370 A1* | 6/2008 | Simon ................. A61K 31/415 424/167.1 |
| 2008/0145371 A1* | 6/2008 | Simon ................. A61K 31/415 424/176.1 |
| 2008/0145420 A1 | 6/2008 | Simon |
| 2010/0322872 A1 | 12/2010 | Perraudin |
| 2013/0210164 A1 | 8/2013 | Gagnon |
| 2013/0338344 A1 | 12/2013 | Ramasubramanyan et al. |
| 2014/0348935 A1 | 11/2014 | Simon |
| 2014/0371431 A1 | 12/2014 | Brown et al. |
| 2015/0005476 A1 | 1/2015 | El Menyawi et al. |
| 2015/0017181 A1 | 1/2015 | Kelly et al. |
| 2015/0030613 A1 | 1/2015 | Aebi et al. |

(Continued)

FOREIGN PATENT DOCUMENTS

| | | |
|---|---|---|
| CN | 1500097 A | 5/2004 |
| EP | 0 413 188 A2 | 2/1991 |

(Continued)

OTHER PUBLICATIONS

Lullau et al., J Biol Chem. Jul. 5, 1996;271(27):16300-9.*
Brandtzaeg, P., Adv Exp Med Biol. 1974;45(0):87-97.*
Radl et al., Proc Soc Exp Biol Med. Nov. 1975;150(2):482-4. abstract only.*
Brandtzaeg, P., Scand J Immunol. 1976;5(4):411-9.*
Underdown et al., J Immunol. Jul. 15, 1992;149(2):487-91.*
Schwartz et al., Diafiltration: A Fast, Efficient Method for Desalting, or Buffer Exchange of Biological Samples, PN 33289 from PALL Life Sciences, Feb. 2003, 6 pages.*
Janeway et al., Immunobiology, 3rd edition, Garland Publishing Inc., 1997, pp. 3:22-3:34 and 8:20-8:21.*
Johansen et al., "Role of J Chain in Secretory Immunoglobulin Formation," Scandinavian Journal of Immunology, vol. 52, 2000, pp. 240-248.

(Continued)

*Primary Examiner* — Michael Szperka
(74) *Attorney, Agent, or Firm* — Birch, Stewart, Kolasch & Birch, LLP

(57) ABSTRACT

The invention relates to methods for preparing compositions comprising secretory-like immunoglobulin, in particular secretory-like IgA and/or secretory-like IgM, and compositions obtainable by the methods.

18 Claims, 13 Drawing Sheets
(3 of 13 Drawing Sheet(s) Filed in Color)
Specification includes a Sequence Listing.

(56) References Cited

U.S. PATENT DOCUMENTS

| | | |
|---|---|---|
| 2015/0056180 A1 | 2/2015 | Corthésy et al. |
| 2017/0051047 A1 | 2/2017 | Berry et al. |
| 2017/0058018 A2 | 3/2017 | Brown et al. |

FOREIGN PATENT DOCUMENTS

| | | |
|---|---|---|
| EP | 0 703 922 A1 | 4/1996 |
| EP | 0839915 A1 | 5/1998 |
| JP | 2000-103800 A | 4/2000 |
| WO | WO 94/29334 A1 | 12/1994 |
| WO | WO 95/04081 A1 | 2/1995 |
| WO | WO 97/25352 A | 7/1997 |
| WO | WO 98/57993 A1 | 12/1998 |
| WO | WO 99/64462 A1 | 12/1999 |
| WO | WO 00/41721 A1 | 7/2000 |
| WO | WO 01/83806 A1 | 11/2001 |
| WO | WO 02/076502 A1 | 10/2002 |
| WO | WO 02/092632 A1 | 11/2002 |
| WO | WO 03/015817 A2 | 2/2003 |
| WO | WO 2004/012763 A1 | 2/2004 |
| WO | WO 2005/047337 A1 | 5/2005 |
| WO | WO 2009/046168 A1 | 4/2009 |
| WO | WO 2009/139624 A1 | 11/2009 |
| WO | WO 2011/131786 A2 | 10/2011 |

OTHER PUBLICATIONS

Sorensen et al., "Structural requirements for incorporation of J chain into human IgM and IgA," International Immunology, vol. 12, No. 1, 2000, pp. 19-27.

Boullier et al., "Secretory IgA-Mediated Neutralization of Shigella flexneri Prevents Intestinal Tissue Destruction by Down-Regulating Inflammatory Circuits," The Journal of Immunology, vol. 183, 2009, pp. 5879-5885.

English translation of the Japanese Office Action, dated Oct. 25, 2016, for Japanese Application No. 2014-560387.

Lindh et al., "Binding of Secretory Component to Human Immunoglobulin M," Eur. J. Biochem., vol. 62, 1976, pp. 271-278.

Aebi et al., "A Protective Epitope of Moraxella catarrhalis Is Encoded by Two Different Genes," Infection and Immunity, vol. 65, No. 11, Nov. 1997, pp. 4367-4377 (Total 12 pages).

Aebi et al., "Phenotypic Effect of Isogenic uspA1 and uspA2 Mutations on Moraxella catarrhalis 035E," Infection and Immunity, vol. 66, No. 7, Jul. 1998, pp. 3113-3119 (Total 8 pages).

Australian Patent Examination Report for Australian Application No. 2013201394, dated Dec. 4, 2013.

Australian Patent Examination Report No. 1, dated Oct. 25, 2013, for Australian Application No. 2013201389.

Bartlett et al., "Antibiotic-Associated Pseudomembranous Colitis Due to Toxin-Producing Clostridia", The New England Journal of Medicine, vol. 298, No. 10, Mar. 9, 1978, pp. 531-534.

Bauer et al., "Alternative strategies for Clostridium difficile infection", International Journal of Antimicrobial Agents, vol. 33, No. S1, 2009, pp. S51-S56.

Blijlevens et al., "Palifermin (recombinant keratinocyte growth factor-1): a pleiotropic growth factor with multiple biological activities in preventing chemotherapy- and radiotherapy-induced mucositis," Annals of Oncology, vol. 18, No. 5, May 2007 (Published online Oct. 9, 2006), pp. 817-826.

Bootsma et al., "Analysis of Moraxella catarrhalis by DNA Typing: Evidence for a Distinct Subpopulation Associated with Virulence Traits," The Journal of Infectious Diseases, vol. 181, 2000 (Electronically published Apr. 13, 2000), pp. 1376-1387.

Brach et al., "Ionizing Radiation Induces Expression of Interleukin 6 by Human Fibroblasts Involving Activation of Nuclear Factor-κB," The Journal of Biological Chemistry, vol. 268, No. 12, Apr. 25, 1993, pp. 8466-8472.

Brooks et al., "Moraxella catarrhalis Binding to Host Cellular Receptors Is Mediated by Sequence-Specific Determinants Not Conserved among All UspA1 Protein Variants," Infection and Immunity, vol. 76, No. 11, Nov. 2008 (Aug. 4, 2008), pp. 5322-5329 (Total 9 pages).

Chinese Office Action and Search Report with English translations thereof, dated May 6, 2014, for Chinese Application No. 201180060034.4.

Cohn et al., "Preparation and Properties of Serum and Plasma Proteins. IV. A System for the Separation into Fractions of the Protein and Lipoprotein Components of Biological Tissues and Fluids," J. Am. Chem. Soc., vol. 68, Mar. 1946, pp. 459-475.

Coia, "What is the role of antimicrobial resistance in the new epidemic of Clostridium difficile?", International Journal of Antimicrobial Agents, vol. 33, No. S1, 2009, pp. S9-S12.

Communication Pursuant to Article 94(3) EPC dated Apr. 23, 2014, in European Patent Application No. 11794757.2.

Communication Pursuant to Article 94(3) EPC dated Dec. 15, 2014, in European Patent Application No. 11794757.2.

Cope et al., "Characterization of the Moraxella catarrhalis uspA1 and uspA2 Genes and Their Encoded Products," Journal of Bacteriology, vol. 181, No. 13, Jul. 1999, pp. 4026-4034 (Total 10 pages).

Cripps et al., "Isolation of Human IgA and IgM from Normal Serum Using Polyethylene Glycol Precipitation and Affinity Chromatography," Journal of Immunological Methods, vol. 57, 1983, pp. 197-204.

Dallas et al., "Binding of Clostridium difficile toxin A to human milk secretory component", J. Med. Microbiol., vol. 47, 1998, pp. 879-888.

Denève et al., "New trends in Clostridium difficile virulence and pathogenesis", International Journal of Antimicrobial Agents, vol. 33, No. S1, 2009, pp. S24-S28.

Deshmane et al., "Monocyte Chemoattractant Protein-1 (MCP-1): An Overview," Journal of Interferon and Cytokine Research, vol. 29, No. 6, 2009, pp. 313-326.

Dewhirst et al., "The Human Oral Microbiome," Journal of Bacteriology, vol. 192, No. 19, Oct. 2010 (Published ahead of print on Jul. 23, 2010), pp. 5002-5017 (Total 17 pages).

Doellgast et al., "Purification of Human IgA by Salt-Mediated Hydrophobic Chromatography," Immunochemistry, vol. 13, 1976, pp. 135-139.

Donadoni et al., "Setting of Methods for Analysis of Mucosal Antibodies in Seminal and Vaginal Fluids of HIV Seropositive Subjects from Cambodian and Italian Cohorts," PLoS ONE, Issue 5, No. 3, Mar. 29, 2010, e9920, pp. 1-16.

Donnelly et al., "Antimicrobial therapy to prevent or treat oral mucositis," The Lancet Infectious Diseases, vol. 3, Jul. 2003, pp. 405-412.

Eibl et al., "Prevention of Necrotizing Enterocolitis in Low-Birth-Weight Infants by IgA-IgG Feeding," The New England Journal of Medicine, vol. 319, No. 1, Jul. 7, 1988, pp. 1-7.

Eldika et al., "Role of nontypeable Haemophilus Influenzae in exacerbations and progression of chronic obstructive pulmonary disease," Current Opinion in Pulmonary Medicine, vol. 12, 2006, pp. 118-124.

Elting et al., "The Burdens of Cancer Therapy: Clinical and Economic Outcomes of Chemotherapy-Induced Mucositis," Cancer, vol. 98, No. 7, Oct. 1, 2003, pp. 1531-1539.

Ertugrul et al., "Comparison of CCL28, interleukin-8, interleukin-1 β and tumor necrosis factor-alpha in subjects with gingivitis, chronic periodontitis and generalized aggressive periodontitis," Journal of Periodontal Research, vol. 48, 2013, pp. 44-51.

Extended European Search Report for European Application No. 10194942.8 dated Oct. 28, 2011.

Extended European Search Report for European Application No. 12158939.4, dated Aug. 17, 2012.

Extended European Search Report dated Jul. 18, 2012, in European Patent Application No. 12158927.9.

Extended European Search Report, dated Aug. 29, 2012, for European Application No. 12158933.7.

Gastmeier et al., "Surveillance of Clostridium difficile-associated diarrhoea with the German nosocomial infection surveillance system KISS (CDAD-KISS)", International Journal of Antimicrobial Agents, vol. 33, No. 81, 2009, pp. S19-S23.

(56) References Cited

OTHER PUBLICATIONS

Gerding, "Clostridium difficile 30 years on: what has, or has not, changed and why?", International Journal of Antimicrobial Agents, vol. 33, No. S1, 2009, pp. S2-S8.

Gorkiewicz, "Nosocomial and antibiotic-associated diarrhoea caused by organisms other than Clostridium difficile", International Journal of Antimicrobial Agents, vol. 33, No. S1, 2009, pp. S37-S41.

Hammarstrom et al., "Systemic and Topical Immunoglobulin Treatment in Immunocompromised Patients," Immunological Reviews, No. 139, 1994, pp. 43-70.

Heiniger et al., "A Reservoir of Moraxella catarrhalis in Human Pharyngeal Lymphoid Tissue," The Journal of Infectious Diseases, vol. 196, Oct. 1, 2007 (Electronically published Aug. 30, 2007), pp. 1080-1087.

Helminen et al., "A Large, Antigenically Conserved Protein on the Surface of Moraxella catarrhalis Is a Target for Protective Antibodies," The Journal of Infectious Diseases, vol. 170, Oct. 1994, pp. 867-872.

Helminen et al., "A Major Outer Membrane Protein of Moraxella catarrhalis Is a Target for Antibodies That Enhance Pulmonary Clearance of the Pathogen in an Animal Model," Infection and Immunity, vol. 61, No. 5, May 1993, pp. 2003-2010 (Total 9 pages).

Hu et al., "Prospective Derivation and Validation of a Clinical Prediction Rule for Recurrent Clostridium difficile Infection", Gastroenterology, vol. 136, No. 4, Apr. 2009, pp. 1206-1214.

International Preliminary Report on Patentability and Written Opinion of the International Searching Authority (Forms PCT/IB/326, PCT/IB/373 and PCT/ISA/237), dated Sep. 18, 2014, for International Application No. PCT/EP2013/054701.

International Preliminary Report on Patentability and Written Opinion of the International Searching Authority issued in International Application No. PCT/EP2013/054722 dated Sep. 18, 2014.

International Preliminary Report on Patentability and Written Opinion of the International Searching Authority dated Sep. 18, 2014, in International Application No. PCT/EP2013/054698.

International Search Report and Written Opinion of the International Searching Authority (Forms PCT/ISA/220, PCT/ISA/210 and PCT/ISA/237) for International Application No. PCT/EP2011/072711 dated May 16, 2012.

International Search Report and Written Opinion of the International Searching Authority (Forms PCT/ISA/220, PCT/ISA/210, and PCT/ISA/237) for International Application No. PCT/EP2013/054722, dated May 7, 2013.

International Search Report and Written Opinion of the International Searching Authority (Forms PCT/ISA/220, PCT/ISA/237 and PCT/ISA/210), dated Jun. 17, 2013, for International Application No. PCT/EP2013/054701.

International Search Report and Written Opinion of the International Searching Authority dated Apr. 10, 2013, in International Application No. PCT/EP2013/054698.

Johnson, "Recurrent Clostridium difficile infection: causality and therapeutic approaches", International Journal of Antimicrobial Agents, vol. 33, No. S1, 2009, pp. S33-S36.

Joost et al., "Characterisation of Clostridium difficile isolates by slpA and tcdC gene sequencing", International Journal of Antimicrobial Agents, vol. 33, No. S1, 2009, pp. S13-S18.

Kanamaru et al., "IgA Fc receptor I signals apoptosis through the FcRγ ITAM and affects tumor growth," Blood, vol. 109, No. 1, Jan. 1, 2007 (Prepublished online: Sep. 25, 2006), pp. 203-211 (Total 10 pages).

Kelly et al., "Clostridium difficile—More Difficult Than Ever", The New England Journal of Medicine, vol. 359, No. 18, Oct. 30, 2008, pp. 1932-1940.

Kobayashi et al., "Separation of Human sIgA1 and sIgA2 by Affinity Chromatography on the Jackfruit Lectin, Jacalin," Adv. Exp. Med. Biol., vol. 216B, 1987, pp. 1193-1197 (Total 6 pages).

Krajci et al., "Molecular Cloning of the Human Transmembrane Secretory Component (POLY-Ig Receptor) and its mRNA Expression in Human Tissues," Biochem. Biophys. Res. Comm., vol. 158, No. 3, Feb. 15, 1989, pp. 783-789.

Kuijper et al., "Emergence of Clostridium difficile-associated disease in North America and Europe", Clinical Microbiology and Infection, vol. 12, Supplement 6, 2006, pp. 2-18.

Leibl et al., "Isolation of Human Serum IgA Using Thiophilic Adsorption Chromatography," Protein Expression and Purification, vol. 6, 1995, pp. 408-410.

Leung et al., "Charge-dependent binding of polymeric IgA, to human mesangial cells in IgA nephropathy," Kidney International, vol. 59, 2001, pp. 277-285.

Liu et al., "CXCL10/IP-10 in infectious diseases pathogenesis and potential therapeutic implications," Cytokine & Growth Factor Reviews, vol. 22, 2011 (Available online Jul. 29, 2011), pp. 121-130.

Lowy et al., "Treatment with Monoclonal Antibodies against Clostridium difficile Toxins", The New England Journal of Medicine, vol. 362, No. 3, Jan. 21, 2010, pp. 197-205.

Luellau et al., "Development of a downstream process for the isolation and separation of monoclonal immunoglobulin A monomers, dimers and polymers from cell culture supernatant," Journal of Chromatography A, vol. 796, 1998, pp. 165-175.

Lüllau et al., "Development of a bioprocess for murine dimeric IgA production," Biotechnology Techniques, vol. 12, No. 6, Jun. 1998, pp. 425-430.

Meier et al., "Moraxella catarrhalis strains with reduced expression of the UspA outer membrane proteins belong to a distinct subpopulation," Vaccine, vol. 23, 2005 (Available online Nov. 10, 2004), pp. 2000-2008.

Meier et al., "Salivary Antibodies Directed against Outer Membrane Proteins of Moraxella catarrhalis in Healthy Adults," Infection and Immunity, vol. 71, No. 12, Dec. 2003, pp. 6793-6798 (Total 7 pages).

Merrigan et al., "New approach to the management of Clostridium difficile infection: colonisation with non-toxigenic C. difficile during daily ampicillin or ceftriaxone administration", International Journal of Antimicrobial Agents, vol. 33, No. S1, 2009, pp. S46-S50.

Miller et al., "Comparison of the Burdens of Hospital-Onset, Healthcare Facility-Associated Clostridium difficile Infection and of Healthcare-Associated Infection due to Methicillin-Resistant . . . ", Infection Control and Hospital Epidemiology, vol. 32, No. 4, Apr. 2011, pp. 387-390.

Monteiro et al., "IgA Fc Receptors," The Annual Review of Immunology, vol. 21, 2003 (First published online as a Review in Advance on Jan. 28, 2003), pp. 177-204 (Total 34 pages).

Mose et al., "Can Prophylactic Application of Immunoglobulin Decrease Radiotherapy-Induced Oral Mucositis?" American Journal of Clinical Oncology, vol. 20, Issue 4, Aug. 1997, pp. 407-411 (14 pages total) (enlarged copies of the tables included).

Moura et al., "Identification of the Transferrin Receptor as a Novel Immunoglobulin (Ig)A1 Receptor and Its Enhanced Expression on Mesangial Cells in IgA Nephropathy," The Journal of Experimental Medicine, vol. 194, No. 4, Aug. 20, 2001, pp. 417-425.

Murphy et al., "Isolation of the outer membrane of Branhamella catarrhalis," Microbial Pathogenesis, vol. 6, 1989, pp. 159-174.

Nicoletti et al., "A rapid and simple method for measuring thymocyte apoptosis by propidium iodide staining and flow cytometry," J. Immunol. Methods, vol. 139, 1991, pp. 271-279.

Nitschmann et al., "107. Vereinfachtes Verfahren zur Gewinnung von humanem Albumin and γ-Globulin aus Blutplasma millets Alkoholfällung," Helvetica Chimica Acta., vol. 37, 1954, pp. 866-873, including English summary.

Oncley et al., "The separation of the Antibodies, Isoagglutinins, Prothrombin, Plasminogen, and β1-Lipoprotein into Subfractions of Human Plasma," J. Am. Chem. Soc., vol. 71, Feb. 1949, pp. 541-550.

Oral Cancer Foundation, "Prevention and Treatment of Oral Mucositis in Cancer Patients," Best Practice, Evidence Based Practice Information Sheets for Health Professionals, vol. 2, Issue 3, 1998, pp. 1-6 (2 pages provided).

Pasquier et al., "Identification of FcαRI as an Inhibitory Receptor that Controls Inflammation: Dual Role of FcRγ ITAM," Immunity, vol. 22, Jan. 2005, pp. 31-42.

(56) References Cited

OTHER PUBLICATIONS

Pejaudier et al., "Preparation of Human IgA as By-Product of Routine Fractionation," Vox Sang., vol. 23, 1972, pp. 165-175.
Pituch, "Clostridium difficile is no longer just a nosocomial infection or an infection of adults", International Journal of Antimicrobial Agents, vol. 33, No. S1, 2009, pp. S42-S45.
Pleass et al., "Identification of Residues in the CH2/CH3 Domain Interface of IgA Essential for Interaction with the Human Fcα Receptor (Fc αR) CD89," J. Biol. Chem, vol. 274, No. 33, Aug. 13, 1999, pp. 23508-23514 (Total 9 pages).
Plevová et al., "Intravenous Immunoglobulin as Prophylaxis of Chemotherapy-Induced Oral Mucositis," Correspondence, Journal of the National Cancer Institute, vol. 89, No. 4, Feb. 19, 1997, pp. 326-327, XP002680345.
Ponka et al., "The transferrin receptor: role in health and disease," The International Journal of Biochemistry & Cell Biology, vol. 31, 1999, pp. 1111-1137.
Que et al., "Fibrinogen and fibronectin binding cooperate for valve infection and invasion in *Staphylococcus aureus* experimental endocarditis," The Journal of Experimental Medicine, vol. 201, No. 10, May 16, 2005, pp. 1627-1635.
Ratner et al., "Synergistic proinflammatory responses induced by polymicrobial colonization of epithelial surfaces," Proceedings of the National Academy of Sciences, vol. 102, No. 9, Mar. 1, 2005, pp. 3429-3434.
Rincon, "Interleukin-6: from an inflammatory marker to a target for inflammatory diseases," Trends in Immunology, vol. 33, No. 11, Nov. 2012, pp. 571-577.
Rodloff et al., "Introduction", International Journal of Antimicrobial Agents, vol. 33, No. 1, 2009, pp. S1-S56 (p. S1 only provided).
Roque-Barreira et al., "Jacalin: An IgA-Binding Lectin," The Journal of Immunology, vol. 134, No. 3, Mar. 1985, pp. 1740-1743.
Ryu et al., "Therapeutic Effects of Recombinant Human Epidermal Growth Factor (rhEGF) in a Murine Model of Concurrent Chemo- and Radiotherapy-Induced Oral Mucositis," Journal of Radiation Research, vol. 51, 2010, pp. 595-601.
Salamone et al., "Promotion of Neutrophil Apoptosis by TNF-α$^1$," J. Immunol, vol. 166, 2001, pp. 3476-3483 (Total 9 pages).
Schedler et al., "Treatment of radiogenic mucositis in patients with head and neck tumors with polyvalent intramuscular immunoglobulin," Tumor Diagnostik and Therapie, vol. 15, No. 5, 1994, pp. 184-191,XP009161354, along with an English summary.
Schettini et al., "Stimulation of neutrophil apoptosis by immobilized IgA," Journal of Leukocyte Biology, vol. 72, Oct. 2002, pp. 685-691.
Singapore Invitation to Respond to Written Opinion dated Oct. 30, 2014, in Singapore Patent Application No. 2013041322.
Sonis, "Mucositis as a biological process: a new hypothesis for the development of chemotherapy-induced stomatotoxicity," Oral Oncology, vol. 34, 1998, pp. 39-43.
Sonis, "Mucositis: the impact, biology and therapeutic opportunities of oral mucositis," Oral Oncology, vol. 45, 2009 (Available online Oct. 13, 2009), pp. 1015-1020.
Spaniol et al., "Outer membrane protein UspA1 and lipooligosaccharide are involved in invasion of human epithelial cells by Moraxella catarrhalis," Microbes and Infection, vol. 10, 2008 (Available online Oct. 2, 2007), pp. 3-11.
Spielberger et al., "Palifermin for Oral Mucositis after Intensive Therapy for Hematologic Cancers," The New England Journal of Medicine, vol. 351, No. 25, Dec. 16, 2004, pp. 2590-2598.
Steinbuch et al., "The isolation of IgG from Mammalian Sera with the Aid of Caprylic Acid," Archives of Biochemistry and Biophysics, vol. 134, 1969, pp. 279-284.
Stokman et al., "Oral mucositis and selective elimination of oral flora in head and neck cancer patients receiving radiotherapy: a double-blind randomised clinical trial," British Journal of Cancer, vol. 88, No. 7, 2003, pp. 1012-1016.
Surawicz et al., "Treatment of refractory and recurrent Clostridium difficile infection", Nature Reviews, vol. 8, Jun. 2011 (published online Apr. 19, 2011), pp. 330-339.
Suzuki et al., "Autocrine production of epithelial cell-derived neutrophil attractant-78 induced by granulocyte colony-stimulating factor in neutrophils," Blood, vol. 99, No. 5, Mar. 1, 2002, pp. 1863-1865.
Takeshita et al., "Intravenous immunoglobulin preparations promote apoptosis in lipopolysaccharide-stimulated neutrophils via an oxygen-dependent pathway in vitro," APMIS, vol. 113, 2005, pp. 269-277.
The Human Microbiome Project Consortium, "Structure, function and diversity of the healthy human microbiome," Nature, vol. 486, Jun. 14, 2012, pp. 207-214.
Van Der Steen et al., "Immunoglobulin A: FcαRI Interactions Induce Neutrophil Migration Through Release of Leukotriene B4," Basic-Alimentary Tract, Gastrogenterology, vol. 137, No. 6, Dec. 2009, pp. 2018-2029.e3.
Von Gunten et al., "Siglec-9 transduces apoptotic and nonapoptotic death signals into neutrophils depending on the proinflammatory cytokine environment," Blood, vol. 106, No. 4, Aug. 15, 2005 (Prepublished online: Apr. 12, 2005), pp. 1423-1431 (Total 10 pages).
Weiss, "Clostridium difficile and fluoroquinolones: is there a link?", International Journal of Antimicrobial Agents, vol. 33, No. S1, 2009, pp. S29-S32.
Wiersma et al., "Structural and Functional Analysis of J Chain-Deficient IgM," J. Immunol., vol. 160, 1998, pp. 5979-5989 (Total 12 pages).
Wijers et al., "Mucositis reduction by selective elimination of oral flora in irradiated cancers of the head and neck: A placebo-controlled double-blind randomized study," International Journal of Radiation Oncology Biology Physics, vol. 50, No. 2, 2001, pp. 343-352.
Wörn et al., "Stability Engineering of Antibody Single-chain Fv Fragments," J. Mol. Biol, vol. 305, 2001, pp. 989-1010.
Atassi et al., "Molecular Immunology," Aug. 31, 1988, pp. 207-210 (Total 6 pages).
Australian Patent Examination Report No. 1 dated Nov. 22, 2013, in Australian Application No. 2013201388.
Balsari et al., "Topical Administration of a Doxorubicin-specific Monoclonal Antibody Prevents Drug-induced Mouth Apoptosis in Mice," British Journal of Cancer, vol. 85, No. 12, 2001, pp. 1964-1967.
Bessen et al., "Passive Acquired Mucosal Immunity to Group A Streptococci by Secretory Immunoglobulin A," Journal of Experimental Medicine, Jun. 1, 1988, vol. 167, No. 6, Jun. 1, 1988, pp. 1945-1950.
Brandtzaeg, "Role of Secretory Antibodies in the Defence Against Infections," Int J. Med. Microbiol., vol. 293, 2003, pp. 3-15.
Cheng et al., "Evaluation of an Oral Care Protocol Intervention in the Prevention of Chemotherapy-induced Oral Mucositis in Paediatric Cancer Patients," European Journal of Cancer, vol. 37, 2001, pp. 2056-2063.
Chinese Office Action and Chinese Search Report, dated Oct. 24, 2016, for Chinese Application No. 201380013075.7 (English Translation only).
Csl Behring, "Company Core Data Sheet for Beriglobin," Sep. 16, 2015, together with an English translation thereof, 17 pages total.
De Wit et al., "Structure of the gene for the human myeloid IgA Fc receptor (CD89)," The Journal of Immunology, vol. 155, 1995, pp. 1203-1209 (Total 8 pages).
Delacroix et al., "Changes in Size, Subclass, and Metabolic Properties of Serum Immunoglobulin A in Liver Diseases and in Other Diseases with High Serum Immunoglobulin A," J Clin. Invest., vol. 71, Feb. 1983, pp. 358-367.
Delacroix et al., "Selective Transport of Polymeric Immunoglobulin A in Bile,"J Clin. Invest., vol. 70, Aug. 1982, pp. 230-241.
English translation of Russian Office Action, dated Nov. 12, 2015, for Russian Application No. 2013132220.
English translation of the Japanese Office Action, dated Nov. 1, 2016, for Japanese Application No. 2014-560392.
Fluckiger et al., "Immunoglobulins Inhibit Adherence and Internalization of *Streptococcus pyogenes* to Human Pharyngeal Cells," Advances in Experimental Medicine and Biology, vol. 418, 1997, pp. 909-911.

(56) References Cited

OTHER PUBLICATIONS

Fluckiger et al., "Immunoglobulins to Group A Streptococcal Surface Molecules Decrease Adherence to and Invasion of Human Pharyngeal Cells," Infection and Immunity, vol. 66, No. 3, Mar. 1998, pp. 974-979.
Frese et al., "Maximizing Mouse Cancer Models," Nature Reviews, vol. 7, Sep. 2007, pp. 645-658.
GE Healthcare Life Sciences, "Mono Q 5/50 GL," Product Data Sheet, Product Code: 17-5166-01, 2016, 1 page.
Gonzalez-Quintela, A. et al, "Serum levels of immunoglobulins (IgG, IgA, IgM) in a general adult population and their relationship with alcohol consumption, smoking and common metabolic abnormalities," Clinical and Experimental Immunology, vol. 151, 2007, pp. 42-50.
Himi et al., "Immune Barrier Changes in Patients with Head and Neck Cancer," Stomato-pharyngology, vol. 6, No. 2, 1994, pp. 71-77, with an English abstract.
Janeway Jr, et al., "Immunobiology," 3rd edition, Garland Publishing Inc., 1997, pp. 8:18-8:19 and 9:19-9:20.
Japanese Office Action, dated Dec. 1, 2015, for Japanese Application No. 2013-543743, with English translation.
Japanese Office Action, dated Nov. 15, 2016, for Japanese Application No. 2014-560388, along with an English translation.
Karolewska et al., "Antibacterial potential of saliva in children with leukemia," Oral Surgery, Oral Medicine, Oral Pathology, Oral Radiology, and Endodontics, vol. 105, No. 6, Jun. 2008, pp. 739-744.
Keefe et al., "Updated Clinical Practice Guidelines for the Prevention and Treatment of Mucositis," Cancer, vol. 109, No. 5, Mar. 1, 2007, pp. 820-831.
Leibl et al., "Method for the Isolation of Biologically Active Monomeric Immunoglobulin A from a Plasma Fraction," Journal of Chromatography B, vol. 678, 1996, pp. 173-180.
Lüer et al., "Topical Curcumin Can Inhibit Deleterious Effects of Upper Respiratory Tract Bacteria on Human Oropharyngeal Cells in Vitro: Potential Role for Patients with Cancer Therapy Induced Mucositis?" Support Care Cancer, vol. 19, 2011 (Published online: May 14, 2010), pp. 799-806.
Malmquist et al., "Characterization of the Influence of Displacing Salts on Retention in Gradient Elution Ion-exchange Chromatography of Proteins and Peptides," Journal of Chromatography, vol. 627, 1992, pp. 107-124 (Total 19 pages).
Morelli et al., "Oral Administration of Anti-Doxorubicin Monoclonal Antibody Prevents Chemotherapy-induced Gastrointestinal Toxicity in Mice," The Journal of Cancer Research, vol. 56, May 1, 1996, pp. 2082-2085 (Total 5 pages).
Olson et al., "Effect of Host Defenses on Clostridium difficile toxin-induced Intestinal Barrier Injury," Trauma Acute Care Surg, vol. 74, No. 4, 2013, pp. 983-990.
Prinsloo et al., "In Vitro Refolding of Recombinant Human Free Secretory Component Using Equilibrium Gradient Dialysis," Protein Expression and Purification, vol. 47, 2006 (Available online Oct. 21, 2005), pp. 179-185.
Qingyi et al., "Biochemical Experiments of Food Products," South China University of Technology Press, Feb. 1, 2012, pp. 24-26 & 30 (Total 6 pages).
Saito et al., "Biological Activity of Secretory IgA, Particularly antibacterial immunity as an example," J. Stomatol. Soc. Jpn., Apr. 26, 1976, vol. 43, No. 2, pp. 107-112.
Steinbuch et al. "Isolement de L'Immunoglobuline IgG Du Plasma Humain a L'Aide de L'Acide Caprylique," Rev. Franc. Etudes Clin. et Biol., vol. XIV, 1969, pp. 1054-1058, with English abstract on p. 1057.
Teschner et al., "A New Liquid, Intravenous Immunoglobulin Product (IGIV 10%) Highly Purified by a State-of-the-art Process," Vox Sanguinis, vol. 92, 2007 (Published online Oct. 24, 2006), pp. 42-55 (Total 15 pages).
Walsh, "Proteins Biochemistry and Biotechnology," John Wiley & Sons, Mar. 2006, pp. 82 (Total 3 pages).

Wright et al, "Neutrophil Function in Inflammation and Inflammatory Diseases," Rheumatology, vol. 49, 2010 (Advanced Access publication Mar. 24, 2010), pp. 1618-1631.
Longet et al., "Human plasma-derived polymeric IgA and IgM antibodies associate with secretory component to yield biologically active secretory-like antibodies," Journal of Biological Chemistry, vol. 288, No. 6, Feb. 8, 2013 (published online Dec. 18, 2012), pp. 4085-4094 (11 pages).
Longet et al., "Reconstituted Human Polyclonal Plasma-derived Secretory-like IgM and IgA Maintain the Barrier Function of Epithelial Cells Infected with an Enteropathogen," Journal of Biological Chemistry, vol. 289, No. 31, Aug. 1, 2014 (published online Jun. 20, 2014), pp. 21617-21626 (11 pages).
Mantis et al., "Secretory IgA's Complex Roles in immunity and Mucosal Homeostasis in the Gut," Mucosal Immunology, vol. 4, No. 6, Nov. 2011 (published online Oct. 5, 2011), pp. 603-611.
Westerhof et al., "Transient Expression of Secretory IgA in Planta is Optimal Using a Multi-Gene Vector and may be Further Enhanced by Improving Joining Chain incorporation," Frontiers in Plant Science, vol. 6, Article 1200, Jan. 11, 2016, pp. 1-12.
Wijburg et al, "Innate secretory antibodies protect against natural *Salmonella typhimurium* infection," J. Experimental Medicine, vol. 203, No. 1, Jan. 3, 2006, pp. 21-26.
International Preliminary Report on Patentability and Written Opinion dated Sep. 18, 2014, in PCT International Application No. PCT/EP2013/054697.
Australian Office Communication dated Nov. 25, 2013, for Australian Application No. 2013201393.
Berdoz et al., "In vitro comparison of the antigen-binding and stability properties of the various molecular forms of IgA antibodies assembled and produced in CHO cells," Proceedings of the National Academy of Sciences, vol. 96, No. 6, Mar. 16, 1999, pp. 3029-3034.
Bonner et al., "Solution Structure of Human Secretory Component and Implications for Biological Function," The Journal of Biological Chemistry, vol. 282, No. 23, Jun. 8, 2007, pp. 16969-16980.
Bonner et al., "Solution structure of recombinant human secretory component and its two- and three-domain fragments by scattering, ultracentrifugation and constrained modeling," Molecular Immunology, vol. 44, Jan. 1, 2007, pp. 156, abstract only 17.
Brandtzaeg, "Mucosal immunity: integration between mother and the breast-fed infant," Vaccine, vol. 21, 2003, pp. 3382-3388.
Chen et al., "A Mouse Model of Clostridium difficile-Associated Disease," Gastroenterology, vol. 135, No. 6, 2008, pp. 1984-1992.
Corthésy et al., "A Pathogen-specific Epitope Inserted into Recombinant Secretory Immunoglobulin A Is Immunogenic by the Oral Route," The Journal of Biological Chemistry, vol. 271, No. 52, Dec. 27, 1996, pp. 33670-33677.
Corthésy et al., "In vitro assembly of secretory immunoglobulin A (sIgA) from IgA and recombinant secretory component," Journal of Cellular Biochemistry, Jan. 5, 1995, pp. 244, abstract only.
Corthesy et al., "Molecular Definition of the Role of Secretory Component in Secretory IgA-Mediated Protection at Mucosal Surfaces," Journal of Allergy and Clinical Immunology, vol. 109, No. 1, Jan. 1, 2002, pp. S113, abstract only.
Corthésy et al., "Secretory Immunoglobulin A: from Mucosal Protection to Vaccine Development," Biological Chemistry, vol. 380, Nov. 1999, pp. 1251-1262.
Corthésy, "Recombinant immunoglobulin A: powerful tools for fundamental and applied research," Trends in Biotechnology, vol. 20, No. 2, Feb. 2002, pp. 65-71.
Corthésy, "Recombinant Secretory Immunoglobulin A in Passive Immunotherapy: Linking Immunology and Biotechnology," Current Pharmaceutical Biotechnology, vol. 4, 2003, pp. 51-67.
Corthésy, "Role of secretory immunoglobulin A and secretory component in the protection of mucosal surfaces," Future Microbiology, vol. 5, No. 5, 2010, pp. 817-829.
Cottet et al., "Microaerophilic Conditions Permit to Mimic in Vitro Events Occurring during in Vivo Helicobacter pylori Infection and to Identify Rho/Ras-associated Proteins in Cellular Signaling," The Journal of Biological Chemistry, vol. 277, No. 37, Sep. 13, 2002, pp. 33978-33986.
Crottet et al., "Mapping the Interaction Between Murine IgA and Murine Secretory Component Carrying Epitope Substitutions Reveals

(56) References Cited

OTHER PUBLICATIONS a Role of Domains II and III in Covalent Binding to IgA," The Journal of Biological Chemistry, vol. 274, No. 44, Oct. 29, 1999, pp. 31456-31462.

Crottet et al., "Secretory Component Delays the Conversion of Secretory IgA into Antigen-Binding Competent F(ab')2: A Possible Implication for Mucosal Defense," The Journal of Immunology, vol. 161, 1998, pp. 5445-5453.

Extended European Search Report dated Aug. 8, 2012, for European Application No. 12158931.1.

Favre et al., "Simplified procedure to recover recombinant antigenized secretory IgA to be used as a vaccine vector," Journal of Chromatography B, vol. 786, 2003, pp. 143-151.

Hendrickson et al., "Lack of Association of Secretory Component with IgA in J Chain-Deficient Mice," The Journal of Immunology, vol. 157, 1996, pp. 750-754.

International Search Report and Written Opinion of the International Searching Authority, dated Apr. 18, 2013, for International Application No. PCT/EP2013/054697.

Kunisawa et al., "A marvel of mucosal T cells and secretory antibodies for the creation of first lines of defense," CMLS Cellular and Molecular Life Sciences, vol. 62, 2005, pp. 1308-1321.

Lüllau et al., "Antigen Binding Properties of Purified Immunoglobulin A and Reconstituted Secretory Immunoglobulin A Antibodies," The Journal of Biological Chemistry, vol. 271, No. 27, Jul. 5, 1996, pp. 16300-16309.

Macpherson et al., "The immune geography of IgA induction and function," Mucosal Immunology, vol. 1, No. 1, Jan. 2008, pp. 11-22.

Phalipon et al., "Monoclonal Immunoglobulin A Antibody Directed against Serotype-specific Epitope of Phalipon Shigella flexneri Lipopolysaccharide Protects against Murine Experimental Shigellosis," The Journal of Experimental Medicine, vol. 182, Sep. 1995 pp. 769-778.

Phalipon et al., "Novel functions of the polymeric Ig receptor: well beyond transport of immunoglobulins," Trends in Immunology, vol. 24, No. 2, Feb. 2003, pp. 55-58.

Phalipon et al "Secretory Component: A New Role in Secretory IgA-Mediated Immune Exclusion In Vivo," Immunity, vol. 17, Jul. 2002, pp. 107-115.

Rindisbacher et al., "Production of Human Secretory Component with Dimeric IgA Binding Capacity Using Viral Expression Systems," The Journal of Biological Chemistry, vol. 270, No. 23, Jun. 9, 1995, pp. 14220-14228.

Watkins et al., "Attenuation of radiation- and chemoradiation-induced mucositis using gamma-D-glutamyl-L-tryptophan (SCV-07)," Oral Diseases, vol. 16, 2010, pp. 655-660.

Wheeler et al., "Immune Components of Colostrum and Milk—A Historical Perspective," Journal of Mammary Gland Biological Neoplasia, vol. 12, Nov. 9, 2007 (published online), pp. 237-247.

Zuercher et al., "Plasma-derived immunoglobulins," Principles of Immunopharmacology: 3rd revised and extended edition, 2011, pp. 271-301.

U.S. Office Action issued in U.S. Appl. No. 15/384,140 dated Sep. 14, 2017.

European Office Communication enclosing Third Party Observation for European Application No. 13708787.0 dated Apr. 7, 2017.

Stubbe et al., "Polymeric IgA Is Superior to Monomeric IgA and IgG Carrying the Same Variable Domain in Preventing Clostridium difficile Toxin A Damaging of T84 Monolayers," J Immunol, vol. 164, No. 4, Feb. 15, 2000, pp. 1952-1960.

U.S. Notice of Allowance dated Nov. 22, 2017, for U.S. Appl. No. 14/383,962.

Kaetzel, "The polymeric immunoglobulin receptor: bridging innate and adaptive immune responses at mucosal surfaces," Immunological Reviews, vol. 206, 2005, pp. 83-99.

\* cited by examiner

1) IgA F5
2) Secretory-like IgA
3) recSC
4) SIgA from milk
5) SIgA from milk, 1:5

A

B

C

COMPOSITIONS COMPRISING SECRETORY-LIKE IMMUNOGLOBULINS

The invention relates to methods for preparing compositions comprising secretory-like immunoglobulin, in particular secretory-like IgA and/or secretory-like IgM, and compositions obtainable by the methods.

IgA is the second most abundant Ig class after IgG in human plasma where it is found at 0.88-4.10 g/L. There are two subclasses of IgA, IgA1 and IgA2 (FIG. 1) (Zuercher A W et al. Plasma derived immunoglobulins. Principles of Immunopharmacology. 3rd ed. Birkhäuser, 2011: p. 271-301) which differ in their disulfide bonds linking heavy and light chains as well as in their antigenic diversity due to significant differences in the hinge region of the molecule. The glycosylation pattern of the two subclasses is different: the heavy chain of both subclasses is N-glycosylated; in contrast, O-glycosylation is found on IgA1 but not IgA2, due to the truncated hinge region of IgA2.

Human IgA is found in two major forms: either circulating in blood/plasma, or secreted to mucosal surfaces. In plasma, IgA is predominantly present as monomers (80-90%) and is produced by bone marrow plasma cells; the major subclass in plasma is IgA1.

The term polymeric IgA (pIgA) describes dimeric, occasionally tetrameric, IgA covalently joined at their "tailpieces" by the Joining (J) chain (FIG. 1).

IgM molecules make up 10% of the total serum Ig content. They are confined predominantly to the intravascular pool and are part of the primary, antigen-specific, humoral immune response; phylogenetically and ontogenetically they are the earliest antibody (Ab) molecules. IgM exists predominantly as a pentamer joined by the J chain and arranged into a planar structure; occasionally, IgM can also be found in a hexameric form lacking the J chain (Zuercher A W et al. Plasma derived immunoglobulins. Principles of Immunopharmacology. 3rd ed. Birkhäuser, 2011: p. 271-301).

Mucosal surfaces of the digestive, respiratory and uro-genital tracts, as well as the ducts of exocrine glands are lined by layers of epithelial cells that form a tight barrier separating the body's internal compartments from the outside environment. In humans, these vast surfaces cover 400 $m^2$, an area that is permanently exposed to exogenous pathogens (Corthésy, B. (2010) Future Microbiol. 5:817-829). The combination of innate and inducible cellular and molecular mechanisms ensures protection against colonization and entry/invasion by microbes. In healthy individuals, secretory IgA (SIgA) is the most abundant antibody (Ab) fulfilling the function of immune exclusion on the luminal side of mucosal surfaces (Macpherson, A. J. et al. (2008) Mucosal Immunol. 1:11-22), whereas secretory IgM Abs take over in IgA-deficient patients. SIgA is synthesised by mucosal plasma cells of the intestinal lamina propria, the upper respiratory tract or the uro-genital tract. SIgA consists of a pIgA dimer, and a highly glycosylated secretory component (SC) of approximately 75 kDa (FIG. 1); similarly pentameric, J chain-containing IgM associated with SC constitutes SIgM. The SC represents the extracellular part of the polymeric Ig receptor (pIgR). pIgR is needed for the trans-epithelial transport of pIgA or pentameric IgM from the site of production to the mucosal surface where the pIgR-pIgA/pIgR-IgM complex is converted to SIgA/SIgM by enzymatic cleavage (Zuercher A W et al. Plasma derived immunoglobulins. Principles of Immunopharmacology. 3rd ed. Birkhäuser, 2011: p. 1-31). Association with SC protects IgA or IgM from proteolytic degradation. SIgA is the predominant Ig in seromucous secretions such as saliva, trachea-bronchial secretions, colostrum, milk, tear fluid, intestinal secretions and uro-genital secretions. It is the most prominent Ig produced at mucosal linings (and thus in the human body); approx. 3-5 g of SIgA is secreted daily into the intestinal lumen. SIgA is thus essential for immune exclusion and to maintain epithelial integrity. SIgM is present at lower levels but fulfills the same immune exclusion functions as SIgA.

For a few pathogens such as Poliovirus, *Salmonella*, or influenza, protection against mucosal infection can be induced by active mucosal immunization with licensed vaccines. However, for the majority of mucosal pathogens no active mucosal vaccines are available. Alternatively, protective levels of Abs might directly be delivered to mucosal surfaces by passive immunization. In nature this occurs physiologically in many mammalian species by transfer of maternal antibodies to their offspring via milk (Brandtzaeg, P. (2003) Vaccine 21:3382-3388). Human and animal studies using passive mucosal immunization have demonstrated that pIgA and SIgA antibody molecules administered by oral, intranasal, intrauterine or lung instillation can prevent, diminish, or cure bacterial and viral infections (Corthésy, B. (2003) Curr. Pharm. Biotechnol. 4:51-67). However, the secretory form of IgA naturally found at mucosal surfaces was rarely used, and large scale production of SIgA is not possible to date. Construction of SIgA with biotechnological methods is challenging but such molecules could have important clinical applications (Corthésy, B. (2002) Trends Biotechnol. 20:65-71). The same also applies to secretory component-containing IgM.

SUMMARY OF THE INVENTION

The inventors have surprisingly found that it is possible to combine plasma-derived J chain-containing immunoglobulin, in particular IgA and/or IgM, with secretory component without the need to first purify the J chain-containing immunoglobulin. This invention opens the door to large-scale production of secretory-like IgA and/or IgM which can be used in medicine, for example for the prevention and treatment of infections on mucosal surfaces in subjects, in particular in human subjects.

One aspect of the invention is a method for producing a composition comprising secretory-like immunoglobulin, in particular IgA and/or IgM, in vitro, comprising the steps of
(a) obtaining a blood-derived protein composition comprising J chain-containing immunoglobulin, in particular IgA and/or IgM, in a non-purified form; and
(b) admixing the composition of step (a) with secretory component.

Preferably, the secretory-like immunoglobulin is secretory-like IgA. Preferably, the composition of step (a) contains at least 5% J chain-containing IgA, more preferably at least 10%, more preferably at least 20%, even more preferably at least 30%, most preferably it will contain at least 50% J chain-containing IgA. Preferably, the composition of step (a) is derived from human blood, e.g. human plasma or fractions thereof enriched for IgA or even J chain-containing IgA, but no purification of J chain-containing IgA is required.

Preferably, the secretory-like immunoglobulin is secretory-like IgM. Preferably, the composition of step (a) contains at least 5% J chain-containing IgM, more preferably at least 10%, more preferably at least 20%, even more preferably at least 30%, most preferably it will contain at least 50% J chain-containing IgM. Preferably, the composition of step (a) is derived from human blood, e.g. human plasma or fractions thereof enriched for IgM or even J chain-containing IgM, but no purification of J chain-containing IgM is required.

The secretory component used in step (b) is preferably recombinant secretory component, more preferably human recombinant secretory component, preferably produced by a mammalian cell line. However, secretory component from a natural source can also be used, such as secretory component purified from milk, saliva, mucus or similar sources.

The molar ratio between secretory component and J chain within IgA dimers/polymers or IgM pentamers in the composition of step (a) ranges between 1:10 and 10:1, preferably between 1:5 and 5:1, more preferably between 1:2 and 2:1.

In another aspect of the invention, the molar ratio between secretory component and J chain within the composition of step a) ranges between 1:10 and 10:1, preferably between 1:5 and 5:1, more preferably between 1:2 and 2:1.

Another aspect of the invention is a composition comprising secretory-like IgA and/or secretory-like IgM or combinations thereof obtainable by a method of the invention. The composition may further comprise a pharmaceutically acceptable carrier or excipient.

A further aspect of the invention is the composition described above for medical use.

DETAILED DESCRIPTION OF THE INVENTION

As already mentioned above, the inventors have surprisingly found that it is possible to combine plasma-derived J chain-containing immunoglobulins, in particular J chain-containing IgA and/or J chain-containing IgM with secretory component without the need to first purify the J chain-containing immunoglobulin. This invention opens the door to large-scale production of secretory-like IgA and/or secretory-like IgM which can be used in medicine, for example for the prevention and treatment of infections on mucosal surfaces in subjects, in particular in human subjects.

One aspect of the invention is a method for producing a composition comprising secretory-like immunoglobulin, in particular secretory-like IgA or secretory-like IgM, in vitro, comprising the steps of
(a) Obtaining a blood-derived protein composition comprising J chain-containing IgA or J chain-containing IgM in a non-purified form,
(b) admixing or combining the composition of step (a) with secretory component.

Preferably, the composition of step (a) contains at least 5% (w/w) J chain-containing IgA, more preferably at least 10%, more preferably at least 20%, even more preferably at least 30%, more preferably at least 50%, most preferably it will contain at least 70% J chain-containing IgA. Preferably, the composition of step (a) is derived from human blood, e.g. human plasma or fractions thereof enriched for IgA or even J chain-containing IgA, but no specific purification steps for J chain-containing IgA dimers or polymers is required. Therefore, the J chain-containing IgA will be in a composition also comprising other proteins such as monomeric IgA, IgM, or IgG. For example, the composition may comprise more than 10% monomeric IgA, and/or more than 10% IgG, and/or more than 10% IgM. While an enrichment for J chain-containing dimeric IgA may happen as part of the processing of human plasma fractions for the purification of plasma proteins such as IgG, albumin, alpha-1 antitrypsin, and coagulation factors, no purification step specifically designed to separate J chain-containing dimeric IgA or polymers from other proteins, like affinity chromatography or size exclusion and selection of the fraction of the relevant molecular mass, is necessary to obtain the composition of step (a).

In another preferred aspect of the invention, the composition of step (a) contains at least 5% (w/w) J chain-containing IgM, more preferably at least 10%, more preferably at least 20%, even more preferably at least 30%, more preferably at least 50%, most preferably it will contain at least 70% J chain-containing IgM. Preferably, the composition of step (a) is derived from human blood, e.g. human plasma or fractions thereof enriched for IgM or even J chain-containing IgM, but no specific purification steps for J chain-containing IgM is required. Therefore, the J chain-containing IgM will be in a composition also comprising other proteins such as IgA or IgG. For example, the composition may comprise more than 10% IgA, and/or more than 10% IgG. While an enrichment for J chain-containing IgM may happen as part of the processing of human plasma fractions for the purification of plasma proteins such as IgG, albumin, alpha-1 antitrypsin, and coagulation factors, no purification step specifically designed to separate J chain-containing IgM from other proteins, like affinity chromatography or size exclusion and selection of the fraction of the relevant molecular mass, is necessary to obtain the composition of step (a).

The term "secretory component" as used herein refers to a protein that specifically binds to J-chain-containing immunoglobulin, and is related to or derivable from or identical to an extracellular portion of the polymeric immunoglobulin receptor (pIgR), preferably a mammalian pIgR, more preferably a primate pIGR, most preferably a human pIgR. Preferably, the secretory component confers increased stability to the J-chain containing immunoglobulin. The secretory component comprised in the composition may be recombinant secretory component, preferably secretory component produced in a mammalian cell line. Secretory component in its traditional, narrow meaning (referred to as "natural secretory component" herein) is the extracellular portion of the polymeric immunoglobulin receptor (pIgR), which usually gets associated during secretion with dimeric or polymeric IgA or pentameric IgM comprising a J chain. J chain-containing IgA/IgM binds to the polymeric immunoglobulin receptor at the basolateral surface of epithelial cells and is taken up into the cell by transcytosis. This receptor complex then transits through the cellular compartments before being transported to the luminal surface of the epithelial cells. The transcytosed IgA/IgM-pIgR complex is then released through proteolysis, and part of the polymeric immunoglobulin receptor (pIgR), referred to as the natural secretory component, stays associated with the J chain-containing IgA/IgM, releasing secretory IgA/IgM. However, there is evidence that reverse transcytosis of IgA, i.e. from the luminal surface to the basolateral surface, can also take place.

The human pIgR is cloned and sequenced, its sequence is available as SwissProt entry P01833, and shown in Seq ID NO: 1. Human pIgR is a glycoprotein with 764 amino acid residues, containing a signal peptide (residues 1 to 18), an extracellular part (residues 19 to 638), a transmembrane region (residues 639 to 661), and a cytoplasmic region (residues 662 to 764). Residues 19 to 603 are thought to associate with J chain-containing IgA as described above, and this part of this glycoprotein is usually referred to as the secretory component (referred to as "natural secretory component" herein).

The secretory component used in the composition of the invention can comprise any extracellular pIgR sequence that is capable of associating with J chain-containing IgA. For example, secretory component may comprise extracellular domains of pIgR from mammalian sources, e.g. from primates, cattle, horses, cats, dogs, rabbits, guinea pigs, rats or mice, or variants thereof. Functional hybrids of the extracellular domains from several mammalian species or variants thereof are also contemplated for use in the invention, e.g. prepared by fusing the immunoglobulin-like domains from different species into a secretory component-like protein. A functional secretory component may also be formed by fusing a selection of immunoglobulin-like domains normally present, e.g. rabbit secretory component is functional being composed of only domains 1, 4 and 5. Preferably, however, the human secretory component or functional variants thereof is used.

Therefore the secretory component used in the composition of the invention preferably comprises residues 19 to 603 of SEQ ID NO: 1 or functional variants thereof. Functional variants may include deletions, insertions, and/or substitutions, preferably substitutions are conservative substitutions, e.g. a basic amino acid residue is substituted for another basic amino acid, a hydrophobic amino acid is substituted for another hydrophobic amino acid, etc. The variant secretory component is at least 50% identical in sequence to residues 19 to 603 of SEQ ID NO: 1, preferably at least 55%, 60%, 65%, 70%, 75%, 80%, more preferably at least 85% or even 90%, even more preferably at least 92%, 94%, 95%, 97%, 98%, or even 99% identical to residues 19 to 603 of SEQ ID NO: 1. Preferably, the secretory component comprises the extracellular portion of the pIgR, more preferably the extracellular portion of the human pIgR, most preferably the secretory component comprises or even consists of residues 19 to 603 of SEQ ID NO: 1.

The skilled person is well aware how to produce the secretory component by recombinant techniques. An example of expression of human secretory component in CHO cells has been described by Phalipon et al (Phalipon A et al (2002) Immunity 17:107-115), but the invention is not limited to secretory component produced by this system. For example, the desired cDNA sequence can be produced synthetically or cloned via RT-PCR, using RNA isolated from cells or tissue expressing pIgR as template. The cDNA can then be inserted into a mammalian expression vector such as pcDNA3—many alternative expression vectors are available. The recombinant expression vector will then be introduced into a suitable host cell line, such as CHO, Cos, HEK293, or BHK. Other cell lines are available and can also be used. Methods for introducing such vectors into a cell line include lipofection, electroporation and other techniques well known to the skilled person. Usually cells harboring the expression vector and expressing the protein of interest are then selected and cloned. Viral expression systems can also be used, for example, vaccinia virus can be used to express proteins at high levels in mammalian cells, baculovirus expression systems can be used to express proteins at high levels in insect cells. Yeast or bacterial expression systems can also be envisaged, and such expression systems are known to the skilled person. Likewise, plant expression systems can also be envisaged, and such systems are known to the skilled person.

The secretory component or variant thereof used in the composition of the invention may also comprise a tag, such as a hexa-Histidine tag, which can aid in the purification of the resulting protein. If such a tag is attached via a cleavable linker, the tag may be cleaved off prior to use in the invention. Similarly, the secretory component may be produced as a fusion protein. Again, a cleavable linker may be used so that the fusion partner may be cleaved off the secretory component prior to use in the invention.

The skilled person can then purify the expressed protein with standard methods. Recombinant secretory component may be purified to high purity with a suitable method, for example size-exclusion and/or ion exchange chromatography. Preferably the final preparation of recombinant secretory component will be essentially free of contaminants, particularly host cell proteins. However, secretory component can also specifically associate with J-chain containing immunoglobulin in unpurified form, thus purification prior to association with the J-chain-containing immunoglobulin is not essential.

The secretory component may also be obtained from a natural source, preferably from milk, saliva or mucus. Preferably the secretory component is of human origin, but secretory component from other species can also be used in the invention.

The molar ratio between secretory component and J chain within IgA dimers/polymers or IgM pentamers in the composition of step (a) ranges between 1:10 and 10:1, preferably between 1:5 and 5:1, more preferably between 1:2 and 2:1.

The molar ratio between secretory component and J chain within the composition of step (a) is between 1:10 and 10:1, preferably between 1:5 and 5:1, more preferably between 1:2 and 2:1.

The amount of secretory component used in step (b) may be at least 1 part (by weight) of secretory component to 50 parts (by weight) of protein in the composition of step (a), preferably at least 1 part to 40, 30, 20, 15, 10, most preferably at least 1 part of secretory component to 5 parts of protein in the composition of step (a).

Another aspect of the invention is a composition comprising secretory-like IgA obtainable by a method of the invention. Yet another aspect of the invention is a composition comprising secretory-like IgM obtainable by a method of the invention. Yet a further aspect is a composition comprising secretory-like IgA and secretory-like IgM obtainable by a method of the invention, for example in a molar ratio of between 10:1 and 1:10, preferably between 5:1 and 1:5, more preferably between 2:1 and 1:2. In another aspect of the invention the combined content of IgA and IgM in the composition exceeds 50%, preferably 60%, more preferably 70%, even more preferably 80%, even more preferably 90%, most preferably it is 100%.

A further aspect of the invention is the composition described above for medical use. For example, the compositions of the invention can be used advantageously to treat necrotizing enterocolitis, and generally infections at mucosal surfaces.

The composition may further comprise one or more pharmaceutically acceptable carrier or excipient, and/or a stabilizer. The composition may be formulated in liquid form, as a syrup, a lotion, an ointment, a powder which may be reconstituted with a liquid prior to administration, a capsule, a pill, a gel, a cream, a jelly, a controlled release formulation, or any other formulation suitable for the intended medical use. For example, for the treatment of GI diseases, the composition may be formulated with a protective coating that dissolves in the desired area of the GI tract to release the composition. The composition may be taken orally, administered topically, enterally, by inhalation, or any other suitable route for the intended use. For oral application acid pump inhibitors may be co-administered.

The proteins in the composition may be concentrated, e.g. using dia/ultrafiltration or other standard methods, prior to being formulated. In addition, the composition may be lyophilized, and then reconstituted with a suitable solution prior to use.

Definitions

The term "secretory-like IgA" or "secretory-like plasma IgA" is intended to encompass J chain-containing (plasma) IgA combined with a protein that is secretory component or a functional variant thereof, which serves to provide some protection from proteolytic digestion. Typically, the J chain-containing IgA will comprise two or four, or even more IgA monomers. Typically, the J chain-containing IgA will be mixed with a secretory component or variant thereof in vitro, i.e. the association between secretory component and J chain-containing IgA takes place in vitro rather than during transcytosis.

The term "secretory-like IgM" is intended to encompass J chain-containing (plasma) IgM combined with secretory component or a functional variant thereof in vitro. Preferably, the J chain-containing IgM will be pentameric IgM.

"Specific purification steps for J chain-containing IgA dimers or polymers" relate to purification steps that would be included in a purification process specifically designed to separate J chain-containing IgA dimers or polymers from other proteins, such as monomeric IgA, other immunoglobulins, and other plasma proteins. Such specific purification steps may, for example, include affinity chromatography with a ligand specifically binding to J chain, or size exclusion chromatography selecting the fractions containing proteins of a molecular weight corresponding to J chain-containing IgA dimers. While the process for preparing the composition from plasma may comprise methods that lead to an enrichment of IgA or even J chain-containing IgA, such as ion exchange chromatography, the J chain-containing IgA is not specifically purified. Thus "J chain-containing IgA in a non-purified form" refers to a composition containing less than 80% J chain-containing IgA, typically less than 70%, 60%, or 50% J chain-containing IgA, it may even contain less than 40%, 30%, 25%, 20%, 15% or even 10% J chain containing IgA.

"Specific purification steps for J chain-containing IgM" relate to purification steps that would be included in a purification process specifically designed to separate J chain-containing IgM from other proteins, such as other immunoglobulins, and other plasma proteins. Such specific purification steps may, for example, include affinity chromatography with a ligand specifically binding to IgM or to J chain, or size exclusion chromatography selecting the fractions containing proteins of a molecular weight corresponding to J chain-containing IgM pentamers. While the process for preparing the composition from plasma may comprise methods that lead to an enrichment of J chain-containing IgM, such as ion exchange chromatography, the J chain-containing IgM is not specifically purified. Thus "J chain-containing IgM in a non-purified form" refers to a composition containing less than 80% J chain-containing IgM, typically less than 70%, 60%, or 50% J chain-containing IgM, it may even contain less than 40%, 30%, 25%, 20%, 15% or even 10% J chain containing IgM.

The term "secretory component" as used herein refers to a protein that specifically binds to J-chain-containing immunoglobulin, and is related to or derivable from or identical to an extracellular portion of the polymeric immunoglobulin receptor (pIgR), preferably a mammalian pIgR, more preferably a primate pIGR, most preferably a human pIgR. Preferably, the secretory component confers increased stability to the J-chain containing immunoglobulin. As detailed above, the most preferred secretory component is human secretory component, e.g. corresponding to residues 19 to 603 of SEQ ID NO: 1. However, amino acid deletions, insertions, substitutions may be included, as long as they lead to a functional protein, i.e. one that is still capable of associating with J chain-containing IgA and preferably conferring protection from proteolytic digestion to it. Homologues from other mammalian species are also included, as are chimeric proteins comprising parts from different species.

The term "% [percent]" when used to describe the content of immunoglobulin in a composition/preparation means weight per weight protein.

LIST OF FIGURES

The patent or application file contains at least one color drawing. Copies of this patent or patent application publication with color drawing will be provided by the USPTO upon request and payment of the necessary fee.

The invention will now be illustrated by the following, non-limiting examples, with reference to the following figures and sequence listing:

FIG. 2 shows Western blots of different IgA preparations, developed with different antibodies:

FIG. 3A shows a flow diagram of how the assay was set up

FIG. 3B shows SC capturing J chain-containing IgA

FIG. 3C shows SC capturing J chain-containing IgM

Figure 5A:
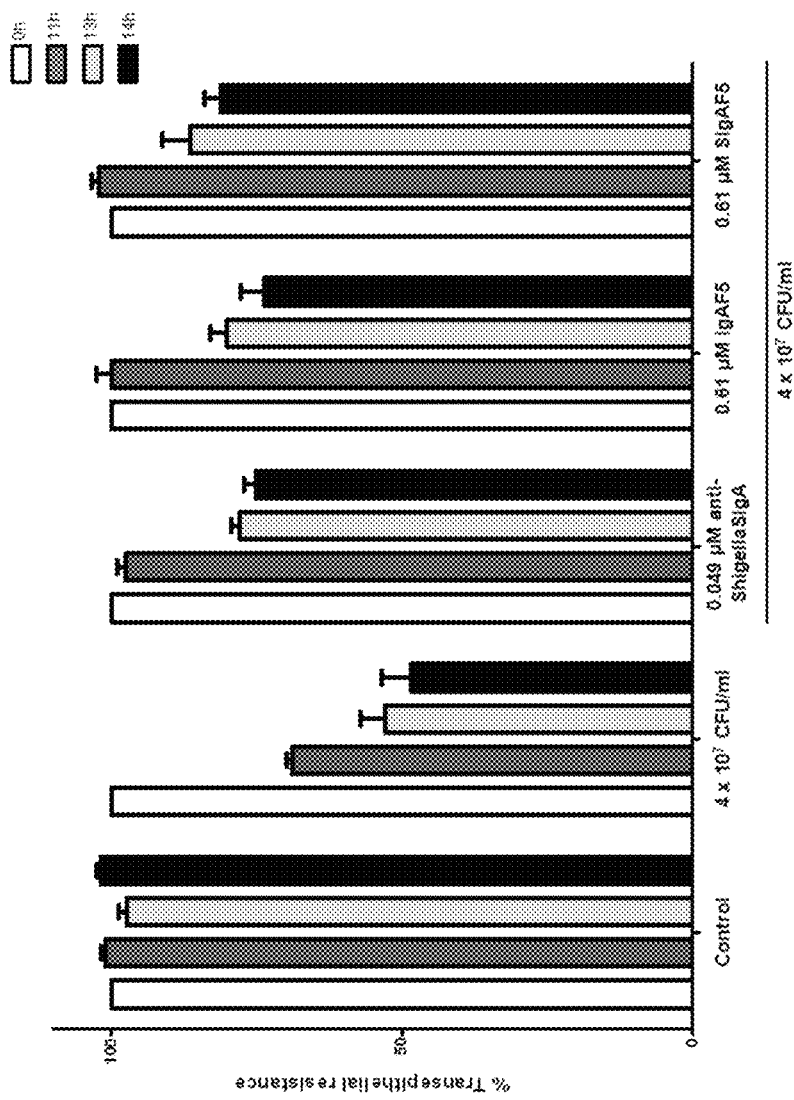
FIG. 5 shows the protection against infection with *Shigella* by different IgA preparations.

FIG. 5A shows the decrease in transepithelial resistance by *Shigella* on polarized Caco-2 monolayers, and the protection from such decrease in TER by anti-*Shigella* SIgA (see Phalipon A et al (1995) J. Exp. Med. 182: 769-778), IgAF5 and SIgAF5.

Figure 5B:
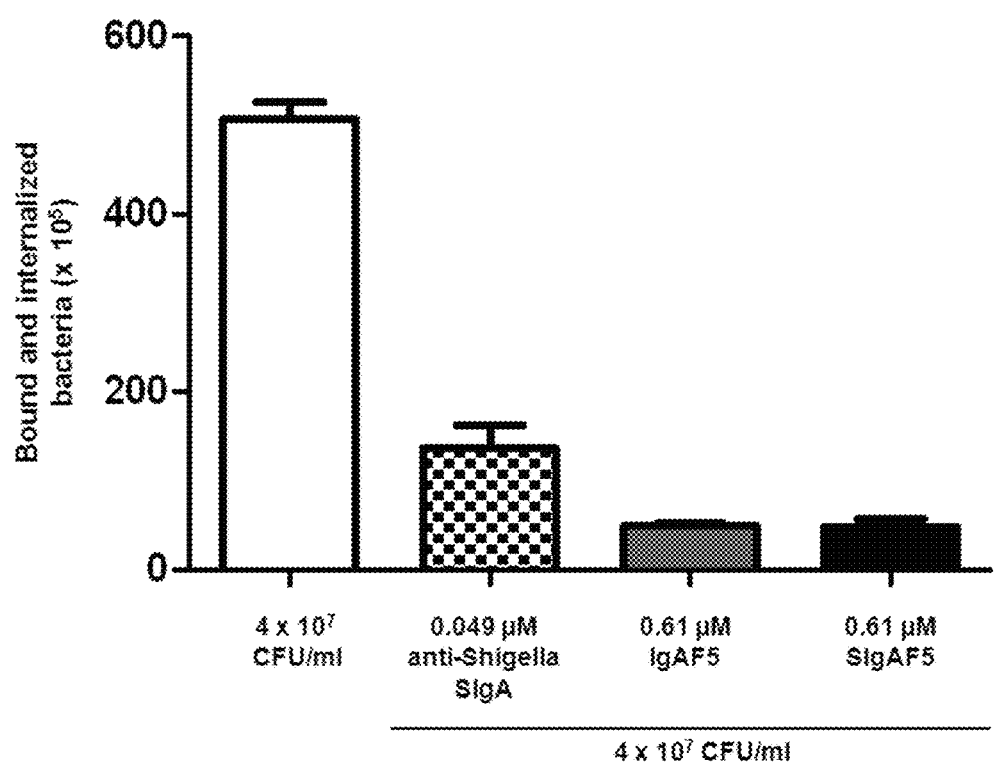

FIG. 5B shows the reduction of bound and internalized bacteria by anti-*Shigella* SIgA, IgAF5 and SIgAF5.

Figure 6:
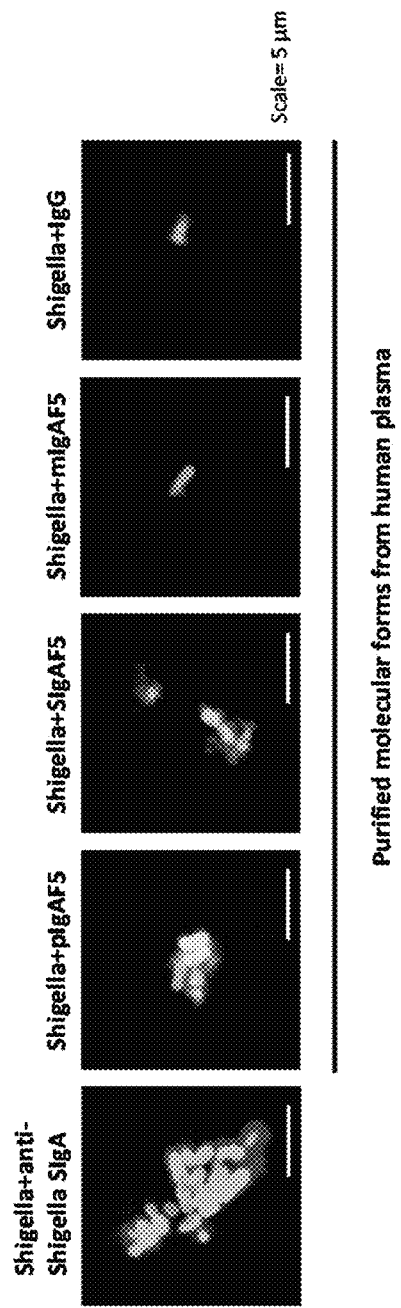

FIG. 6 shows images of *Shigella* in immune complexes obtained after incubation with anti-*Shigella* SIgA (SIgAC5) used as a positive control, and plasma-derived polymeric IgAF5, SIgAF5, monomeric IgAF5 and IgG.

Figure 7:
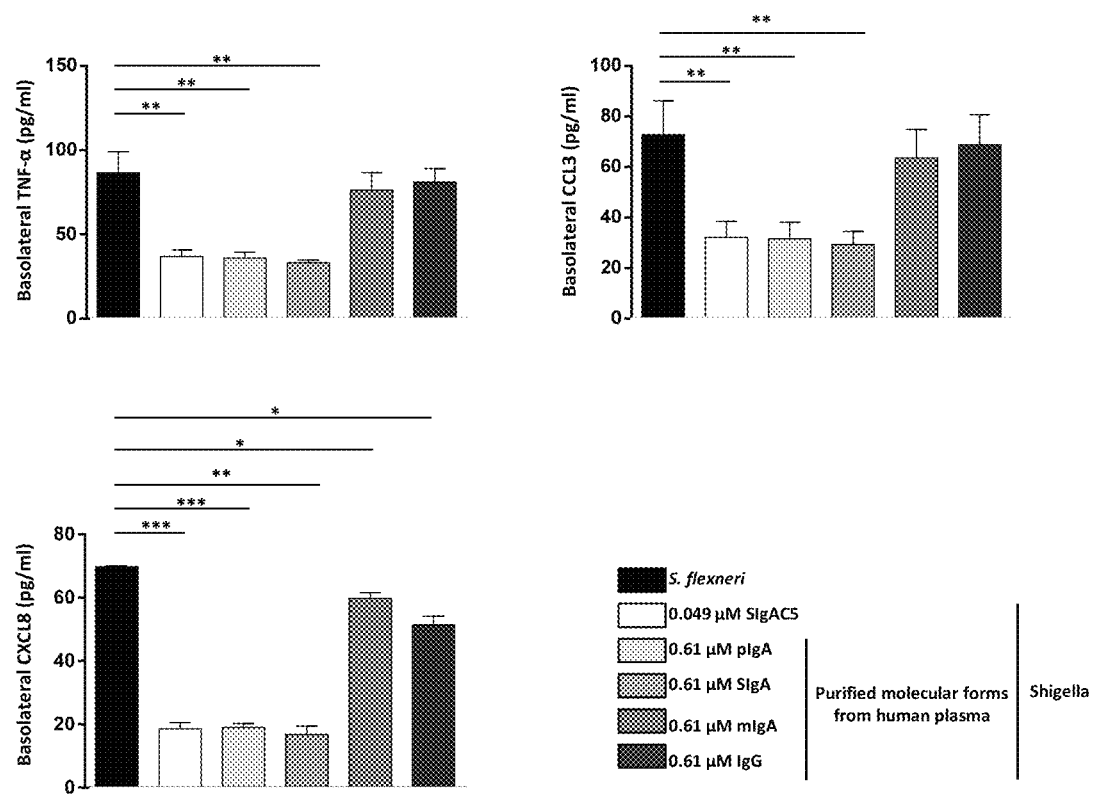

FIG. 7 shows secretion of cytokine TNF-α and chemokines CXCL8 and CCL3 by polarized Caco-2 epithelial cell monolayers exposed to *Shigella* alone or in complex with various Abs.

Figure 8:
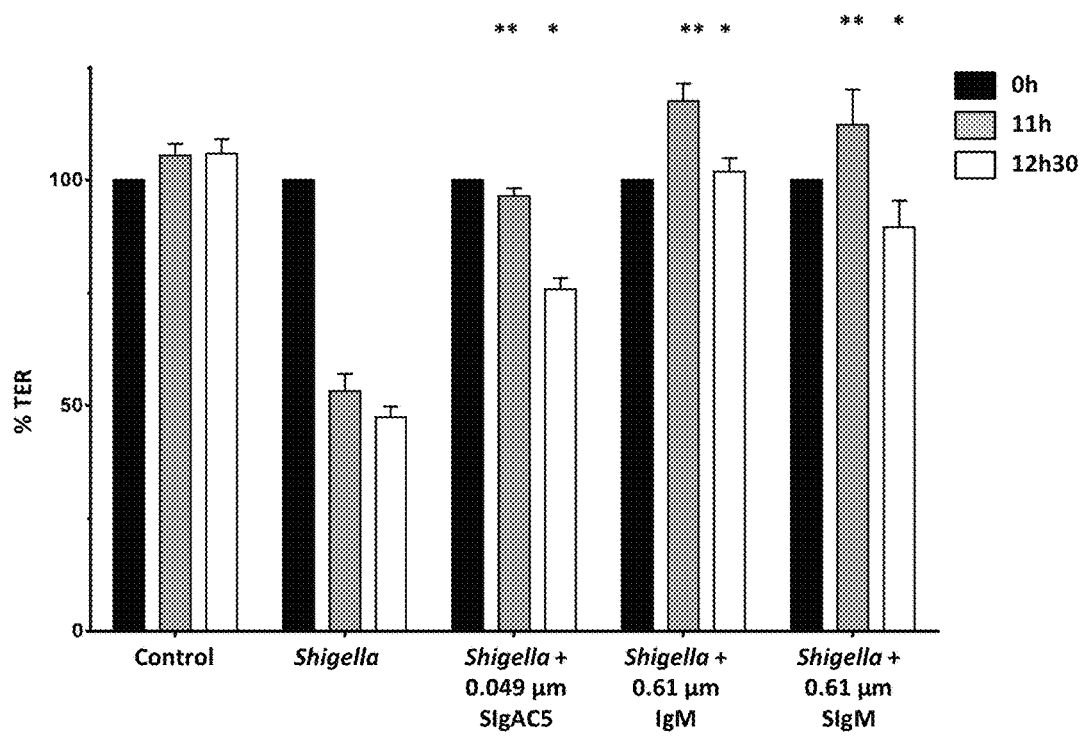

FIG. 8 shows the protection against infection with *Shigella* by pentameric IgM and SIgM preparations.

FIG. 8 shows the decrease in transepithelial resistance by *Shigella* on polarized Caco-2 monolayers, and the protection from such decrease in TER by anti-*Shigella* SIgA (see Phalipon A et al (1995) J. Exp. Med. 182: 769-778), IgM and SIgM.

SEQ ID NO: 1 shows the protein sequence of human pIgR.

EXAMPLES

Example 1: Western Blot of IgA Preparations from Plasma Mixed with Recombinant Secretory Component Materials and Methods 1.1 IgA Preparation from Plasma by Affinity Chromatography and/or by Sequential Elution of MPHQ Column Human plasma IgA was purified by affinity chromatography using CaptureSelect Human IgA resin (Bioaffinity Company BAC, Naarden, Netherlands) according to the resin manufacturer's protocol using 3 different sources of plasma IgA as starting material, namely cryo-depleted plasma, re-solubilised cold ethanol fractionation paste, or a strip fraction from an anion-exchange (AIEX) chromatography column obtained by sanitizing said column, according to the commercially applied IgG purification process of CSL Behring AG (Berne, Switzerland). Briefly, cryo-depleted pool plasma, re-solubilised paste or AIEX strip fraction was diluted in phosphate buffered saline (PBS) to an IgA concentration of approximately 1 mg/mL and then loaded onto a PBS-equilibrated CaptureSelect Human IgA column, without exceeding the IgA binding capacity of the column. After loading the column was washed with PBS, and IgA was eluted with glycin buffer at pH 3. The eluate was adjusted with 0.5M Tris (pH 8) to pH 4.5 and concentrated up to 16 mG/mL protein in PBS. SIgA from human milk was purified by the same method.

From the AIEX chromatography step of the IVIg manufacture process of CSL Behring AG (Berne, Switzerland), fraction F4 was obtained after a post-wash of the Macro-Prep High Q (Bio-Rad, Hercule, Calif.) column with 10 mM phosphate/30 mM acetate at pH 6.5 by elution with 55 mM tartrate/5 mM acetate at pH 7.6. Then, fraction F5 was eluted with 50 mM phosphate/25 mM citrate at pH 5.0. F4 and F5 were brought to approximately 1 mG/mL in PBS by ultra-/diafiltration, and then depleted of IgG by affinity chromatography using IgSelect resin (GE Healthcare, Glattbrugg, Switzerland). IgAF4 was directly harvested in the flowthrough of the IgSelect chromatography of F4 load. To obtain IgAF5, the IgSelect flowthrough of F5 load was depleted of IgM by affinity chromatography using CaptureSelect Human IgM resin (Bioaffinity Company BAC). IgAF4 and IgAF5 were brought to final concentrations by ultra-/diafiltration.

1.2 IgM Preparation from Plasma by Affinity Chromatography

Human plasma IgM was purified by affinity chromatography using CaptureSelect Human IgM resin (Bioaffinity Company BAC, Naarden, Netherlands) according to the resin manufacturer's protocol using the same 3 different sources as starting material as described in section 1.1 for IgA, namely cryo-depleted plasma, re-solubilised cold ethanol fractionation paste, or a strip fraction from an anion-exchange (AIEX) chromatography column obtained by sanitizing said column, according to the commercially applied IgG purification process of CSL Behring AG (Berne, Switzerland). Briefly, cryo-depleted pool plasma, re-solubilised paste or AIEX strip fraction was diluted in phosphate buffered saline (PBS) to an IgM concentration of approximately 1 mg/mL and then loaded onto a PBS-equilibrated CaptureSelect Human IgM column, without exceeding the IgM binding capacity of the column. After loading the column was washed with PBS, and IgM was eluted with glycin buffer at pH 3. The eluate was adjusted with 0.5M Tris (pH 8) to pH 4.5 and concentrated up to 10 mG/mL protein in PBS.

1.3. Western Blots

SDS-PAGE and electrotransfer onto nitrocellulose (NC) membranes were carried out using the Mini-Cell system from Invitrogen (Carlsbad, Calif.), according to the manufacturer's protocols. Briefly, samples were denatured in sample buffer under reducing or non-reducing conditions, respectively, and electrophoretically separated on pre-cast gradient gels, NuPAGE Novex Bis-Tris 4-12% 1.0 mm 10 well, using NuPAGE MOPS Electrophoresis Buffer (Invitrogen). Wet transfer onto NC membranes (0.2 μm) was performed with the XCell II Blot Module (Invitrogen) and NuPAGE Transfer Buffer. The membranes were then blocked for 30 min in PBS-0.5% Tween 20 solution (PBS-T) containing 4% Rapilait skim milk powder (Migros, Switzerland). For immunoblotting polyclonal rabbit antibodies were used: 1) rabbit anti-human alpha chain (Dako, horseradish peroxidase (HRP)-conjugated: 1/5,000 dilution); 2) rabbit anti-human J chain (BioGenex, Fremont, Calif.; 1/300 dilution), followed by secondary anti-rabbit HRP-conjugated antiserum (Sigma; 1/10,000 dilution); 3) rabbit anti-human SC (Dako; 1/5000 dilution), followed by secondary anti-rabbit HRP-conjugated antiserum (Sigma; 1/10,000 dilution). All incubations were performed in PBS-T containing 4% milk powder at ambient temperature for 1-2 hours. After final washing with PBS-T, immunodetection on membranes was revealed by chemiluminescence and digitally recorded in an ImageQuant LAS 4000 system (GE Healthcare Lifesciences).

1.4 Association of Plasma Derived IgA with Recombinant Secretory Component

Secretory-like IgA was obtained by combining in vitro 100 mg of IgAF5 with 4 mg of recombinant human secretory component (recSC). Association was performed in PBS for 30 min at room temperature as previously described in (Crottet, P., and Corthésy, B. (1998) J. Immunol. 161:5445-5453).

1.5 Size Exclusion Chromatography (SEC) Fractionation

IgAF5 comprising secretory-like IgA (associated in vitro with recSC) was injected at 200 μG/20 μL into an Agilent Technologies 1050 HPLC system for size exclusion chromatography at a flowrate of 1.5 mL/min over a TSKgel G3000SWXL 7.8 mm ID×30 cm column (Tosoh Bioscience). Fractions of 0.75 mL were collected between 8.0 and 13.5 min retention time in intervals of 30 sec.

Results

The results are shown in FIG. 2. FIG. 2A demonstrates a comparison of IgA purified by affinity chromatography from plasma, from re-solubilised paste and from AIEX strip fraction or by sequential elution to obtain IgAF5 as described in 1.1 with SIgA from human milk. Secretory component was found in SIgA from milk but not in any of the IgA fractions purified from human plasma. All preparations contained the same amount of IgA heavy chain/alpha-chain. As expected, SIgA from milk contained the highest amount of J chain as essentially all IgA molecules are expected to be present as J chain-containing dimers. The amount of J chain and thus J chain-containing IgA dimers in IgA purified from plasma was low. This is expected as only a small portion of plasma IgA is present in dimeric form. A similar content of J chain was observed in IgA purified from re-solubilised paste. Surprisingly an increased fraction of IgA was present as J chain-containing dimers in the column strip fraction as evidenced by the increased amount of J chain. Surprisingly, this was further increased in IgAF5. This accumulation occurred without application of a specific process step for enrichment.

Figure 1:
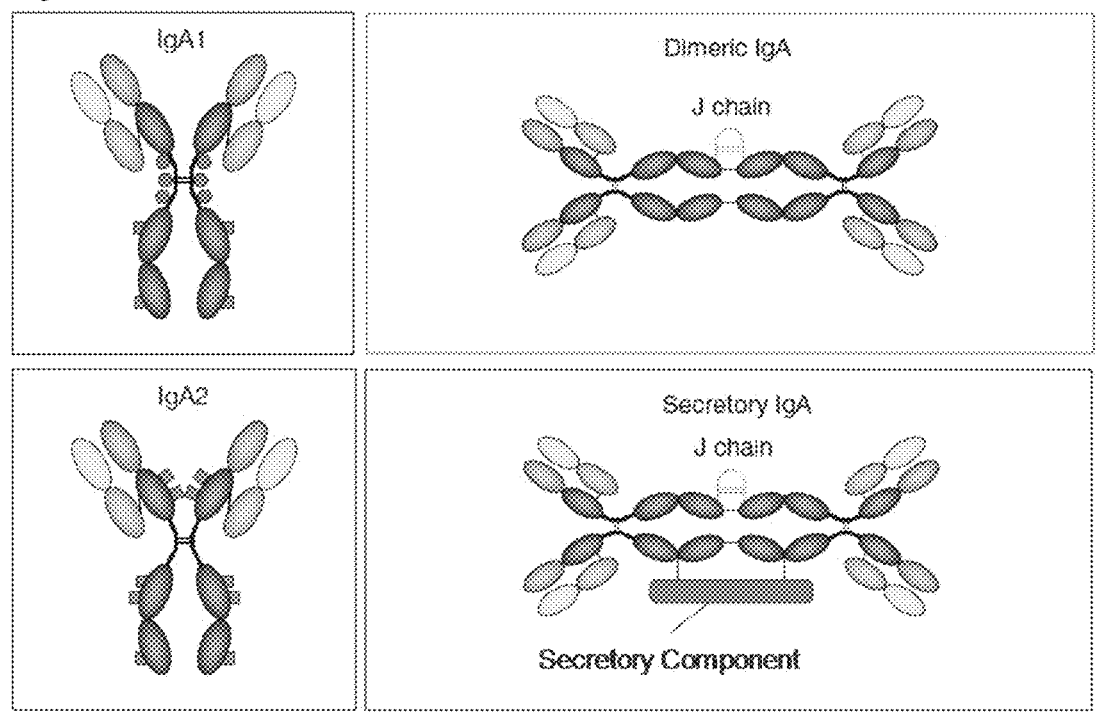
FIG. 1 shows a diagram of the structure of monomeric, dimeric and J chain-containing secretory IgA.
Figure 2A:
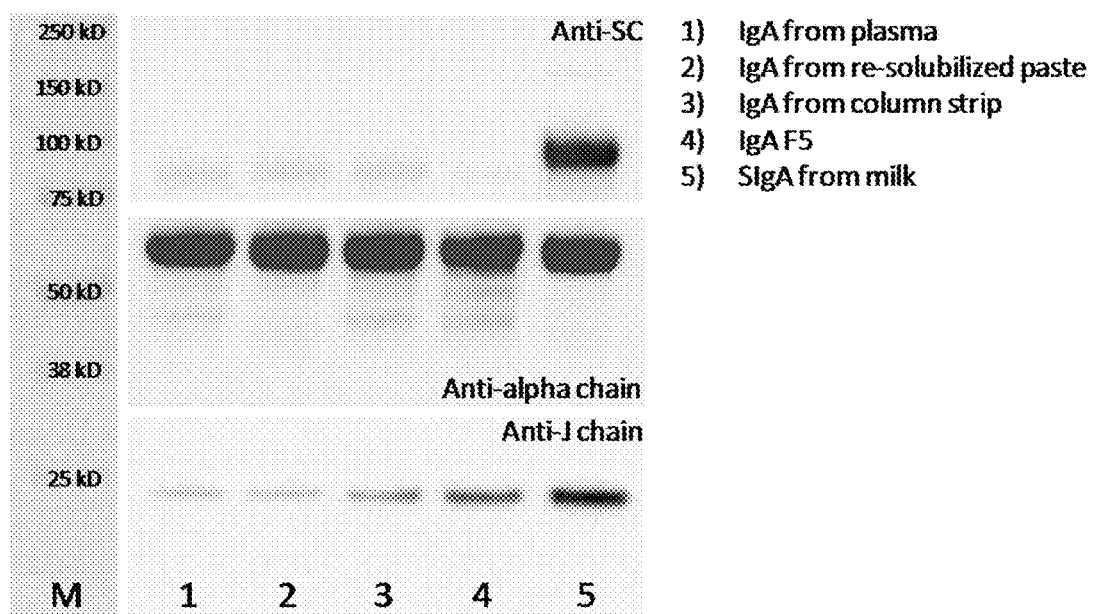
FIG. 2A shows a Western blot of different IgA preparations, developed with anti-α chain, anti-J chain or anti-secretory component antibody.
Figure 2B:
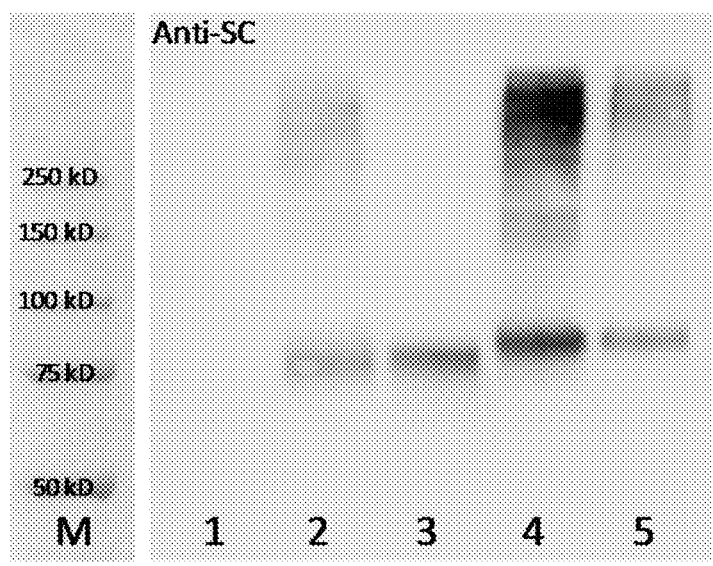
FIG. 2B shows a Western blot of different secretory-like and secretory IgA preparations, developed with anti-secretory component antibody.

FIG. 2B shows that no secretory-component containing IgA was present in IgAF5. After association with recSC free recSC (75 kDa) and dimeric IgA associated with recSC were found. Indeed the secretory-like plasma IgA appeared similar to SIgA from milk. It was estimated that in the preparation of IgAF5 used in the shown experiment the content of J chain-containing IgAF5 was about 20%. Indeed, the signal strength observed in lane 2 was comparable to the signal of 1:5-diluted human milk SIgA.

Figure 2C:
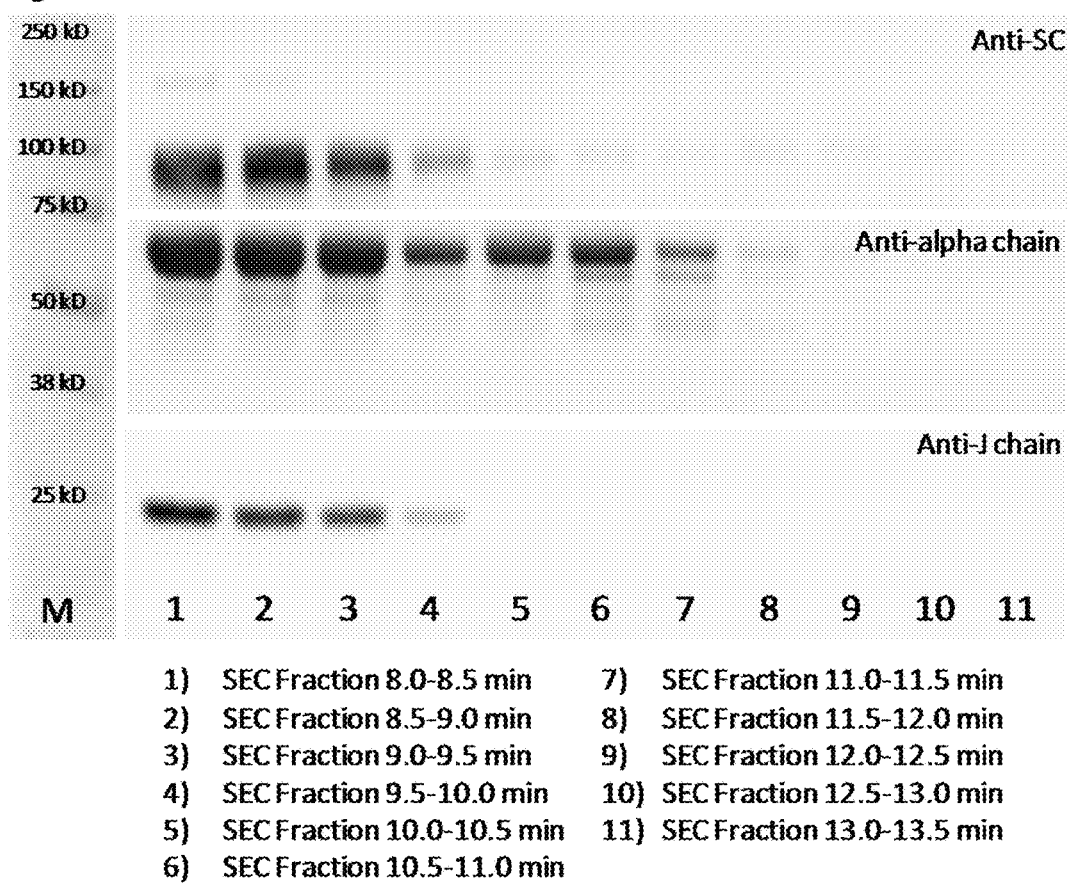
FIG. 2C shows a Western blot of different size exclusion chromatography fractions of secretory-like IgAF5, developed with antibodies to secretory component, α chain and J chain.

FIG. 2C shows the content of SC, IgA alpha chain and J chain in fractions obtained by size-exclusion chromatography of secretory-like IgAF5. recSC was observed in early fractions corresponding to high molecular weight forms of IgA-likely polymeric and dimeric forms. Appearance of SC coincided with appearance of J chain, indicating that indeed the SC-containing fraction of IgAF5 was the dimeric, J chain-containing fraction. In addition IgA alpha-chain was detected in fractions of smaller molecular weight, likely comprising the monomeric fraction of IgAF5; these fractions were devoid of SC and J chain. These data demonstrate that recSC admixed with plasma-derived IgA containing monomeric and dimeric forms of IgA specifically associated with the dimeric, J chain-containing forms of IgA.

Figure 2D:
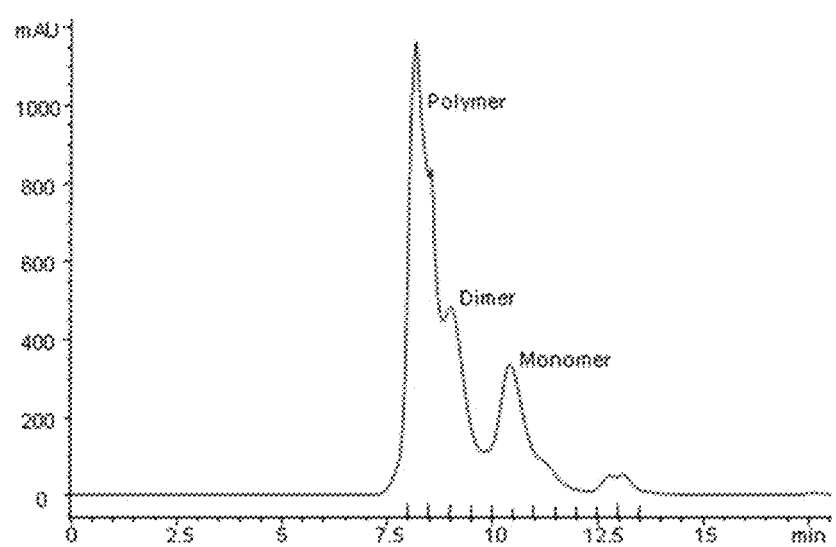
FIG. 2D shows a chromatogram of a size exclusion chromatography run of secretory-like IgAF5.

FIG. 2D shows the chromatogram of the SEC run during which fractions were collected between retention time 8.0 min and 13.5 min. Peaks representing IgA polymers, dimers and monomers are indicated.

Example 2: Dot Blot Re-Association Assay (DORA)

Figure 3:
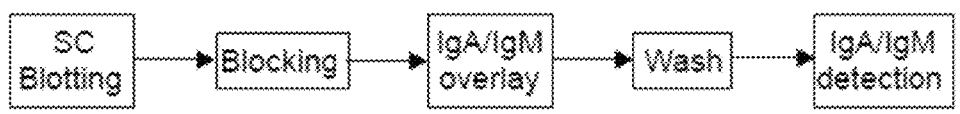
FIG. 3 shows dot blots, using immobilized secretory component.
Figure 3:
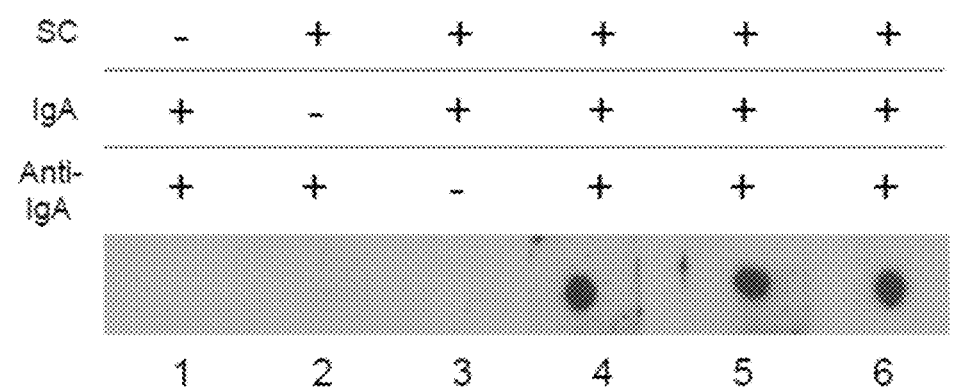
Figure 3:
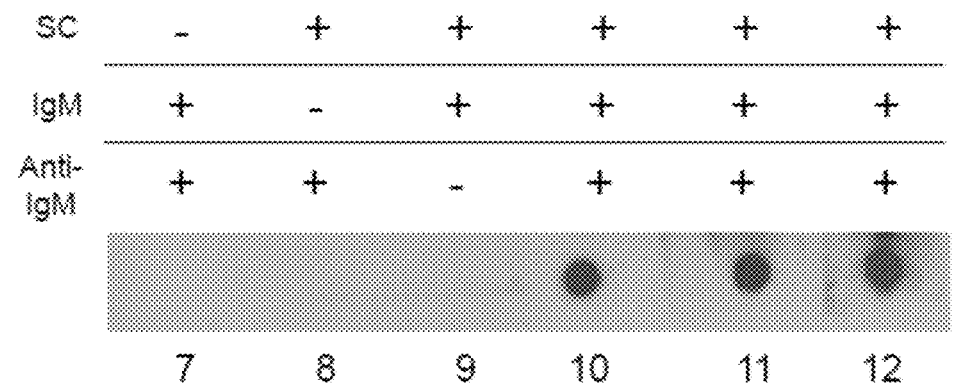

A dot-blot re-association assay was used to show the association of immobilised secretory component with plasma-derived IgA or IgM in vitro. Briefly, as shown in FIG. 3A, secretory component was dotted onto blotting membranes; non-specific binding sites were blocked. Thereafter plasma-derived IgA (FIG. 3B) or IgM (FIG. 3C) obtained by affinity chromatography from plasma (lane 4), from re-solubilised paste (lane 5) or from AIEX strip fraction (lane 6) obtained as described in 1.1 and 1.2 were applied to the membrane. After washing off unbound IgA or IgM, bound IgA/IgM was detected as described briefly below.

DORA was carried out essentially as described (Rindisbacher, L. et al (1995) J. Biol. Chem. 270:14220-14228), with the following modifications: Blotting membranes consisted of polyvinylidone fluoride (PVDF) polymer, blocking solution was phosphate-buffered saline-0.05% Tween-20 (PBS-T) containing 1% bovine serum albumin (BSA), crude preparations enriched in IgA were used for overlay incubation in 200 µl of PBS-T containing 0.1% BSA, and detection antibodies were directly coupled to HRP.

The results for IgA are shown in FIG. 3B. Immobilised secretory component was capable of capturing plasma-derived IgA. Similar to what is shown in FIG. 2C this demonstrates that recSC associated with plasma-derived IgA dimers.

The results for IgM are shown in FIG. 3C. Immobilised secretory component was capable of capturing plasma-derived IgM. This demonstrates that recSC associated with plasma-derived IgM.

Example 3: Digestion of Secretory-Like IgA and Secretory-Like IgM with Intestinal Washes In order to prove a functional advantage of association of purified secretory component with J chain-containing IgA and IgM, respectively, IgA and IgM were prepared as described in paragraph 1.1 and 1.2. Secretory-like IgA was obtained by enriching J chain-containing IgA using size-exclusion chromatography and combining in vitro 10 µg thereof with 2.5 µg of recombinant human secretory component (hSCrec). Secretory-like IgM was obtained by enriching pentameric IgM using size-exclusion chromatography and combining in vitro 25 µg thereof with 2.5 µg of recombinant human secretory component (hSCrec). Association was performed in PBS for 30 min at room temperature as previously described (Crottet, P., and Corthésy, B. (1998) J. Immunol. 161:5445-5453). Integrity and proper assembly of the molecules into possibly covalent complexes were examined by SDS-PAGE under non-reducing and reducing conditions, followed by Western blotting and immunodetection with antiserum specific for hSC as indicated above.

Collection of intestinal washes from BALB/c mice (4-6 weeks old) was done according to the published procedure (Crottet, P., and Corthésy, B. (1998) J. Immunol. 161:5445-5453). For in vitro digestion, 120 ng of purified J chain-containing IgA and reconstituted secretory-like IgA were mixed (or not) with 1 or 2 µl of intestinal washes in a final volume of 20 µl of PBS and incubated at 37° C. for various periods of time as indicated in FIG. 4 (T=time in hours). For in vitro digestion of IgM, 250 ng purified IgM and secretory-like IgM were mixed with 4 µl of intestinal washes. Reactions were stopped by the addition of 2 µl of Complete™ protease inhibitor mixture (Roche Applied Science, Rotkreuz, Switzerland), and kept frozen until analysis by Western blot detecting the reduced form of heavy chain of the antibody.

Figure 4A:
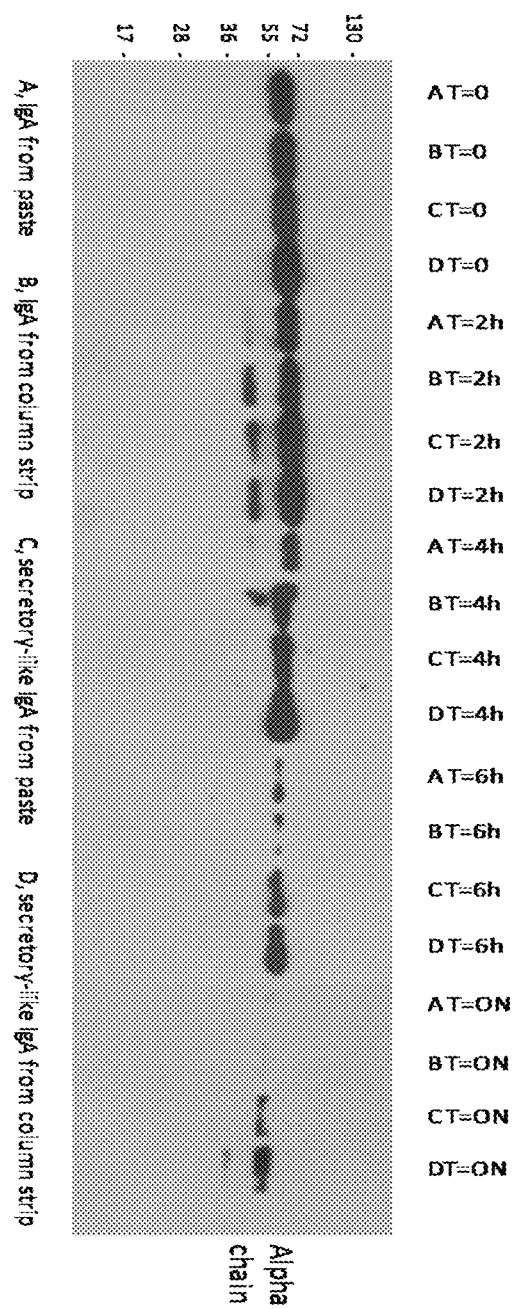
FIG. 4 shows Western blots of time course experiments of different IgA preparations (A) or IgM preparations (B) incubated with intestinal washes. The blots were developed using anti-heavy chain antibodies.
Figure 4B:
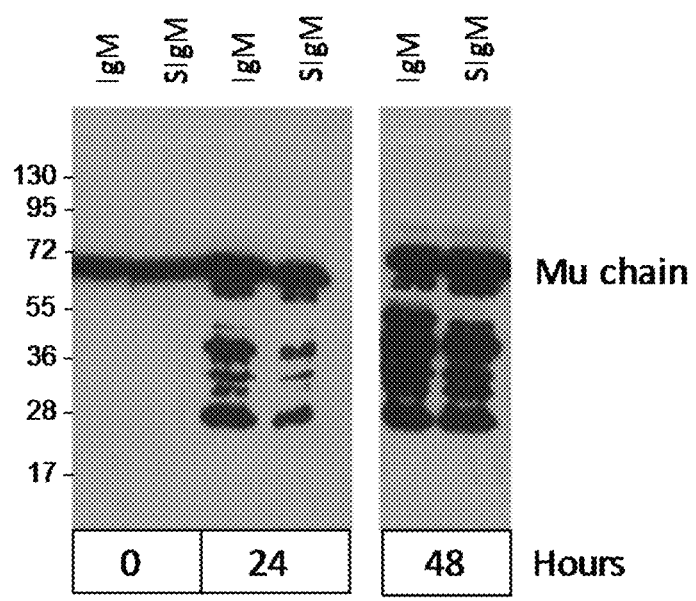

The results are shown in FIGS. 4A and B. IgA from re-solubilized paste and from column strip obtained as described in 1.1. and IgM from column strip as described in 1.2. were either used as such or both after association with recSC to form secretory-like IgA (FIG. 4A) or secretory-like IgM (FIG. 4B). For IgA, after 4 hours of digestion with intestinal enzymes the signal of non-associated IgA started to decrease, indicative of proteolytic digestion; the effect was stronger after 6 hours and after overnight digestion, no intact IgA alpha-chain was detected by Western blot. In contrast, secretory-like IgA was much less sensitive to digestion by intestinal proteases and even after overnight exposure a significant portion of IgA alpha-chain within secretory-like IgA remained intact.

For IgM (FIG. 4B) a comparison of IgM and freshly associated secretory-like IgM (SIgM) with the same preparations after 24 h and 48 h of digestion is shown. Appearance of degraded mu-chain fragments occurred more rapidly and more extensively for IgM compared to SIgM, confirming for IgM—similar as for IgA—that association with recSC provided improved structural stability.

Overall, this demonstrates that the specific association with recSC provided improved structural stability, and will make the digestion-prone plasma IgA molecules fit for mucosal application, e.g. via the oral route.

Example 4: Shigella flexneri

The human colonic adenocarcinoma epithelial Caco-2 cell line (American Type Tissue Collection) was seeded on polyester Snapwell filters (diameter, 12 mm; pore size, 0.4 µm; Corning Costar) as described (Crottet, S., Corthésy-Theulaz, I., Spertini, F., and Corthésy, B. (2002) J. Biol. Chem. 277:33978-33986). The integrity of the polarized Caco-2 cell monolayer was checked by measuring the transepithelial electrical resistance (TER) using a Millicell-ERS device (Millipore). TER values of well-differentiated monolayers ranged between 450-550$\Omega \times cm^2$.

$2 \times 10^7$ bacteria (Phalipon A. et al (1995) J. Exp. Med. 182:769-778) were mixed with 100 µg of IgA, 125 µg of secretory-like IgA, 275 µg IgM or 300 µg SIgM in a final volume of 500 µl of plain DMEM (P-DMEM: DMEM complemented with 10 mM HEPES, 20 µg/ml transferrin, 2 mM glutamine, 1% non-essential amino acids, 1 mM sodium pyruvate) and incubated for 1 h at RT under gentle agitation. The mixtures were resuspended in P-DMEM to infect polarized Caco-2 cell monolayers.

1 h before the use of polarized Caco-2 cell monolayers, C-DMEM was replaced by P-DMEM in both the apical and basolateral compartments. Apical medium was then replaced by 500 µl of bacterial suspensions ($2 \times 10^7$ bacteria) as such or in combination with the antibody. TER values were measured at selected time-points from the beginning of the infection onward.

To quantify bacteria that had adhered and infected the cells, Caco-2 cells in filters were washed three times with PBS, cells were incubated in 500 µl of cold lysis buffer [10 mM Tris-HCl (pH 7), 0.2% Nonidet P-40, 50 mM NaCl, 2 mM EDTA (pH 8)] for 5 min on ice and lysed by up-and-down pipetting. Serial dilutions ($10^{-2}$-$10^{-6}$) of cell lysates were applied onto LB agar plates and after 24 h of incubation at 37° C., colony-forming units (CFU) were determined by eye counting of duplicate plates.

To examine the integrity of Caco-2 cell monolayers, Snapwells were washed with PBS, prior to fixation overnight with 5 ml of 4% paraformaldehyde at 4° C. After washing with PBS, filters were permeabilized and non-specific binding sites were blocked using PBS containing 5% FCS and 0.2% Triton X-100 (PBS-Tr) for 30 min at RT. All antibodies were diluted in PBS-Tr. Filters were incubated with rabbit anti-human ZO-1 (1/200, Invitrogen) for 2 h at RT, washed in PBS, followed by goat anti-rabbit IgG conjugated with Alexa Fluor® 647 (1/100, Invitrogen) for 90 min at RT. To visualize cells, filters were finally incubated with 100 ng/ml of 4',6-diamidino-2-phenylindole (DAPI) in PBS (Invitrogen) for 30 min. Filters were cut out of their holders, and mounted in Vectashield solution for observation using a Zeiss LSM 710 Meta confocal microscope (Carl Zeiss, Germany) equipped with either a 10× or a 40× objective. Images were processed using the Zeiss ZEN 2009 light software.

To examine Shigella-IgA complexes, bacteria constitutively expressing green fluorescent protein were used and the formation of immune complexes was verified after incubation with biotinylated mouse anti-human IgA1/IgA2 (1/10, BD) for 30 min at RT under gentle agitation, followed by cyanine 5-conjugated Streptavidin (1/400, GE HealthCare) for 30 min at RT under gentle agitation. Three washes with PBS were performed between each step and all antibodies were diluted in PBS/5% FCS. Labeled immune complexes were laid onto glass slides (Thermo Scientific), mounted and immediately visualized using a Zeiss LSM 710 Meta confocal microscope (Carl Zeiss, Germany) equipped with a 63× objective. Images were processed with the Zeiss ZEN 2009 light software.

Human CXCL8 (IL-8), TNF-α, and CCL3 (MIP-3α) in the basolateral compartment of polarized Caco-2 cell monolayers were quantitated by ELISA with commercial kits (BD Biosciences and R&D Systems, respectively).

Results

Exposure of the polarized intestinal epithelial cell monolayer to Shigella led to disruption of the integrity of the monolayer, evidenced by a decrease of TER (FIG. 5A), massive invasion, evidenced by elevated bacterial counts found in association with the epithelial cells (FIG. 5B), and by a visibly compromised cell monolayer as observed by laser scanning confocal microscopy. Addition of secretory-like IgA delayed and partially inhibited the destruction of the monolayer, indicated by a significant inhibition of the reduction of TER (FIG. 5A), by a reduction in the number of epithelial cell-bound bacteria (FIG. 5B), and by a more preserved cell monolayer integrity in analysis by confocal microscopy.

Association of Shigella-specific monoclonal SIgA SIgAC5, polymeric IgA and secretory-like IgA resulted in the formation of immune aggregates (FIG. 6) of multiple bacteria, in contrast to monomeric IgA and IgG that coated the bacterium only (FIG. 6). It is likely that bacterial aggregation by the specific mAb and plasma-derived pIgA and secretory-like IgA contributed to the reduction of bacterial adhesion to Caco-2 cells observed in FIG. 5B. The same three antibody preparations markedly reduced the production of pro-inflammatory cytokines/chemokines by Caco-2 cells, while monomeric IgAF4 and IgG had no (TNF-α and CCL3) or weak (CXCL8) effects (FIG. 7). This indicates that neutralization of Shigella by secretory and polymeric IgA decreases the responsiveness of Caco-2 cells, ultimately contributing to the overall anti-inflammatory properties of IgA.

Protection of the polarized Caco-2 cell monolayer from infection with Shigella was similarly achieved with IgM and secretory-like IgM, to a level at least similar to that recovered when using specific SIgAC5 (FIG. 8). Maintenance of TER for at least 12 h30 indicated that the IgM isotype possesses neutralizing properties protecting the Caco-2 monolayer from damages induced by exposure to Shigella.

Example 5: Prevention of Recurrence of Clostridium difficile Infection (CDI)

The composition of the invention is used in a mouse model of Clostridium difficile infection.

C57BL/6 mice are treated with a mixture of oral antibiotics (kanamycin, gentamicin, colistin, metronidazole, and vancomycin) for 3 days as previously described (Chen X, et al. Gastroenterology 2008 December; 135(6):1984-92). Two days later, they are given parenteral clindamycin phosphate (10 mg/kg s.c.) [Day −1]. One day later [Day 0] they are challenged by gavage with $0.5 \times 10^5$ cfu of toxinogenic C. difficile strain 10465. A moderate to fulminant colitis develops 1 to 5 days after the administration of C. difficile. Untreated, this progresses rapidly into severe and fatal colitis in the majority of animals. To treat primary infection animals receive vancomycin, for 5 days after *C. difficile* challenge, and the animals are monitored for mortality, as well as the presence or absence of severe CDI with diarrhea. Animals judged to be in a moribund state are euthanized by a single injection of sodium pentobarbital. To study recurrence of CDI animals surviving primary *C. difficile* challenge are maintained under observation until day 28. Animals are weighed 3 times weekly from day 7 to 28. After cessation of vancomycin treatment animals receive IgA or secretory-like IgA (400 mg/kg body weight via the oral route) for 5 days starting the day after the last dose of vancomycin.

Result

Animals treated with vancomycin survive the primary infection with *C. difficile*. However, a significant proportion of animals—up to 70%—succumb to recurrence of *C. difficile* infection within 3-4 days after termination of vancomycin treatment. In contrast, recurrence of infection is prevented if animals are treated with secretory-like IgA via the oral route. Plasma IgA alone is not effective (or at least not as effective) as secretory-like IgA in preventing recurrence of *C. difficile* infection.

Alternatively, the composition is used in a model of oral mucositis similar as described in Watkins et al (Oral Dis 2010, 16:655-660).

Appropriately formulated IgA preparations (or vehicle solution for control) are given prophylactically (e.g. starting at day −3) three times daily to Syrian Golden Hamsters for the entire duration of the study up to day 28. In a model of acute radiation-induced mucositis, on day 0 one everted buccal cheek pouch is irradiated (40 Gy), the other cheek pouch is left untreated for control. Alternatively, in a model of fractionated radiation-induced mucositis, a cumulative dose of 60 Gy is applied, partitioned into eight fractions of 7.5 Gy as described in (Watkins, Oral Dis 2010, 16:655-660). In yet another model of combined cisplatin and acute radiation-induced mucositis, disease is induced by a combination of cisplatin (5 mg/kg) and 35 Gy radiation on day 0. Clinical evaluation of oral mucositis and monitoring of body weight is done daily, starting on Day 6 until the end of the study, typically on Day 28. The scoring system is described in (Watkins Oral Dis, 2010 16:655-660). In addition, tissue and plasma samples are collected and appropriately processed throughout the study for histological analyses, determination of inflammatory markers in plasma and for gene expression studies of various tissues.

Results

Untreated/vehicle treated animal develop oral mucositis, disease peaks around day 16-18, spontaneous healing, evidenced by a regression of the mucositis, starts around day 18-20. Animals treated with IgA and in particular with Secretory-like IgA have significantly lower mucositis scores compared to control animals and lose less weight, paralleled by less severe histological findings and reduced levels of inflammatory markers (including but not limited to inflammatory cytokines and chemokines). Reduction of inflammation and promotion of wound-healing is confirmed at the level of mRNA expression by gene-expression analysis techniques.

---

The invention claimed is:

1. A method for producing a composition comprising secretory-like immunoglobulin in vitro, comprising the steps of
    (a) obtaining from normal human donors a plasma-derived protein composition comprising J chain-containing immunoglobulin in a form not purified by size exclusion chromatography,
    (b) admixing the composition of step (a) with recombinant mammalian secretory component suitable for human administration.

2. The method of claim 1, wherein the secretory-like immunoglobulin is secretory-like IgA and/or secretory-like IgM.

3. The method of claim 1 or claim 2, wherein the composition of step (a) contains at least 5% J chain-linked IgA.

4. The method of claim 3, wherein the composition of step (a) contains at least 10% J chain-linked IgA.

5. The method of claim 3, wherein the composition of step (a) contains at least 20% J chain-linked IgA.

6. The method of claim 3, wherein the composition of step (a) contains at least 30% J chain-linked IgA.

7. The method of claim 3, wherein the composition of step (a) contains at least 50% J chain-linked IgA.

8. The method of claim 1, wherein the secretory component is human secretory component.

9. The method of claim 1, wherein the secretory component is produced in a mammalian cell line.

10. The method of claim 1, wherein the secretory component is the extracellular portion of the polymeric immunoglobulin receptor pIgR.

11. The method of claim 1, wherein in step (b) the molar ratio between added secretory component and J chain within IgA dimers/polymers ranges between 1:10 and 10:1.

12. The method of claim 11, wherein the ratio ranges between about 1:5 and 5:1.

13. The method of claim 12, wherein the ratio ranges between about 1:2 and 2:1.

14. The method of claim 1, wherein the composition of step (a) contains J chain-linked IgA.

15. The method according to claim 1, wherein the J chain-containing immunoglobulin is enriched without size exclusion chromatography before admixing the composition of step (a) in step (b).

16. A method for producing a composition comprising secretory-like immunoglobulin in vitro, comprising the steps of
    (a) obtaining from normal human donors a plasma-derived protein composition comprising J chain-containing immunoglobulin in a form not purified by size exclusion chromatography,
    (b) admixing the composition of step (a) with recombinant mammalian secretory component suitable for human administration, and
    (c) adding one or more pharmaceutically acceptable carrier or excipient.

17. The method according to claim 16, wherein the J chain-containing immunoglobulin is enriched without size exclusion chromatography before admixing the composition of step (a) in step (b).

18. The method of claim 16, wherein the composition of step (a) contains J chain-linked IgA.

* * * * *

SEQUENCE LISTING

```
<160> NUMBER OF SEQ ID NOS: 1

<210> SEQ ID NO 1
<211> LENGTH: 764
<212> TYPE: PRT
<213> ORGANISM: Homo sapiens

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
```

-continued

```
                165                 170                 175
Ile Asp Ser Ser Gly Tyr Val Asn Pro Asn Tyr Thr Gly Arg Ile Arg
            180                 185                 190
Leu Asp Ile Gln Gly Thr Gly Gln Leu Leu Phe Ser Val Val Ile Asn
        195                 200                 205
Gln Leu Arg Leu Ser Asp Ala Gly Gln Tyr Leu Cys Gln Ala Gly Asp
    210                 215                 220
Asp Ser Asn Ser Asn Lys Lys Asn Ala Asp Leu Gln Val Leu Lys Pro
225                 230                 235                 240
Glu Pro Glu Leu Val Tyr Glu Asp Leu Arg Gly Ser Val Thr Phe His
            245                 250                 255
Cys Ala Leu Gly Pro Glu Val Ala Asn Val Ala Lys Phe Leu Cys Arg
        260                 265                 270
Gln Ser Ser Gly Glu Asn Cys Asp Val Val Asn Thr Leu Gly Lys
    275                 280                 285
Arg Ala Pro Ala Phe Glu Gly Arg Ile Leu Leu Asn Pro Gln Asp Lys
    290                 295                 300
Asp Gly Ser Phe Ser Val Val Ile Thr Gly Leu Arg Lys Glu Asp Ala
305                 310                 315                 320
Gly Arg Tyr Leu Cys Gly Ala His Ser Asp Gly Gln Leu Gln Glu Gly
            325                 330                 335
Ser Pro Ile Gln Ala Trp Gln Leu Phe Val Asn Glu Glu Ser Thr Ile
        340                 345                 350
Pro Arg Ser Pro Thr Val Val Lys Gly Val Ala Gly Ser Val Ala
    355                 360                 365
Val Leu Cys Pro Tyr Asn Arg Lys Glu Ser Lys Ser Ile Lys Tyr Trp
    370                 375                 380
Cys Leu Trp Glu Gly Ala Gln Asn Gly Arg Cys Pro Leu Leu Val Asp
385                 390                 395                 400
Ser Glu Gly Trp Val Lys Ala Gln Tyr Glu Gly Arg Leu Ser Leu Leu
            405                 410                 415
Glu Glu Pro Gly Asn Gly Thr Phe Thr Val Ile Leu Asn Gln Leu Thr
        420                 425                 430
Ser Arg Asp Ala Gly Phe Tyr Trp Cys Leu Thr Asn Gly Asp Thr Leu
    435                 440                 445
Trp Arg Thr Thr Val Glu Ile Lys Ile Ile Glu Gly Glu Pro Asn Leu
    450                 455                 460
Lys Val Pro Gly Asn Val Thr Ala Val Leu Gly Glu Thr Leu Lys Val
465                 470                 475                 480
Pro Cys His Phe Pro Cys Lys Phe Ser Ser Tyr Glu Lys Tyr Trp Cys
            485                 490                 495
Lys Trp Asn Asn Thr Gly Cys Gln Ala Leu Pro Ser Gln Asp Glu Gly
        500                 505                 510
Pro Ser Lys Ala Phe Val Asn Cys Asp Glu Asn Ser Arg Leu Val Ser
    515                 520                 525
Leu Thr Leu Asn Leu Val Thr Arg Ala Asp Glu Gly Trp Tyr Trp Cys
    530                 535                 540
Gly Val Lys Gln Gly His Phe Tyr Gly Glu Thr Ala Ala Val Tyr Val
545                 550                 555                 560
Ala Val Glu Glu Arg Lys Ala Ala Gly Ser Arg Asp Val Ser Leu Ala
            565                 570                 575
Lys Ala Asp Ala Ala Pro Asp Glu Lys Val Leu Asp Ser Gly Phe Arg
        580                 585                 590
```

```
Glu Ile Glu Asn Lys Ala Ile Gln Asp Pro Arg Leu Phe Ala Glu Glu
            595                 600                 605
Lys Ala Val Ala Asp Thr Arg Asp Gln Ala Asp Gly Ser Arg Ala Ser
    610                 615                 620
Val Asp Ser Gly Ser Ser Glu Glu Gln Gly Gly Ser Ser Arg Ala Leu
625                 630                 635                 640
Val Ser Thr Leu Val Pro Leu Gly Leu Val Leu Ala Val Gly Ala Val
                645                 650                 655
Ala Val Gly Val Ala Arg Ala Arg His Arg Lys Asn Val Asp Arg Val
            660                 665                 670
Ser Ile Arg Ser Tyr Arg Thr Asp Ile Ser Met Ser Asp Phe Glu Asn
            675                 680                 685
Ser Arg Glu Phe Gly Ala Asn Asp Asn Met Gly Ala Ser Ser Ile Thr
        690                 695                 700
Gln Glu Thr Ser Leu Gly Gly Lys Glu Glu Phe Val Ala Thr Thr Glu
705                 710                 715                 720
Ser Thr Thr Glu Thr Lys Glu Pro Lys Lys Ala Lys Arg Ser Ser Lys
                725                 730                 735
Glu Glu Ala Glu Met Ala Tyr Lys Asp Phe Leu Leu Gln Ser Ser Thr
            740                 745                 750
Val Ala Ala Glu Ala Gln Asp Gly Pro Gln Glu Ala
    755                 760
```